(12) United States Patent
Jackels et al.

(10) Patent No.: US 10,004,647 B2
(45) Date of Patent: *Jun. 26, 2018

(54) APPARATUS AND METHOD FOR TRANSFERRING PARTICULATE MATERIAL

(71) Applicant: The Procter & Gamble Company, Cincinnati, OH (US)

(72) Inventors: Hans Adolf Jackels, Euskirchen (DE); Harald Hermann Hundorf, Bonn (DE); Siegfried Link, Schleiden/Oberhausen (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/131,286

(22) Filed: Apr. 18, 2016

(65) Prior Publication Data

US 2016/0228299 A1  Aug. 11, 2016

Related U.S. Application Data

(60) Continuation of application No. 14/077,487, filed on Nov. 12, 2013, now Pat. No. 9,340,363, which is a
(Continued)

(30) Foreign Application Priority Data

Dec. 2, 2009  (EP) .................................... 09177725

(51) Int. Cl.
*B65G 29/00* (2006.01)
*A61F 13/15* (2006.01)
(Continued)

(52) U.S. Cl.
CPC ...... *A61F 13/15658* (2013.01); *A61F 15/001* (2013.01); *B65G 29/00* (2013.01); *B65G 29/02* (2013.01); *B05C 1/08* (2013.01)

(58) Field of Classification Search
CPC .......... A61F 13/15577; A61F 13/15617; A61F 13/15658; A61F 15/001; B65G 29/00;
(Continued)

(56) References Cited

U.S. PATENT DOCUMENTS 1,733,997 A 10/1929 Marr
1,734,499 A 11/1929 Marinsky
(Continued)

FOREIGN PATENT DOCUMENTS

CA 2001370 4/1990
CA 2291997 6/2000
(Continued)

OTHER PUBLICATIONS

American Chemical Society publication entitled "Contact Angle, Wettability and Adhesion", Advances in Chemistry Series 43, Chapter 7, edited by Robert F. Gould (Copyright 1964).
(Continued)

*Primary Examiner* — Nicolas A Arnett
(74) *Attorney, Agent, or Firm* — Charles R. Matson

(57) ABSTRACT

An apparatus for transferring, at high speed and in a very effective and accurate manner, particulate material from a feeder into reservoirs of a moving endless surface, e.g. a drum, by use of a pressure means, e.g. a specific three-dimensional plate, for applying pressure onto said particulate material present between said plate and said moving endless surface, and then transferring the particulate material with said moving endless surface with reservoirs to a substrate; the apparatus and method being particularly useful for the production of absorbent structures for absorbent articles.

16 Claims, 7 Drawing Sheets

Related U.S. Application Data division of application No. 12/958,484, filed on Dec. 2, 2010, now Pat. No. 8,590,582.

(51) Int. Cl.
- *A61F 15/00* (2006.01)
- *B65G 29/02* (2006.01)
- *B05C 1/08* (2006.01)

(58) Field of Classification Search
CPC ......... B65G 29/02; B05C 1/08; B05C 1/0813; B05C 1/0826
USPC .......................................... 141/11–12, 71, 81
See application file for complete search history.

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Morin |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,381,783 A | 5/1983 | Elias |
| 4,388,075 A | 6/1983 | Mesek et al. |
| 4,437,294 A * | 3/1984 | Romagnoli ............ B65B 1/366 222/332 |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievet et al. |
| 4,527,990 A | 7/1985 | Sigl |
| 4,541,871 A | 9/1985 | Obayashi et al. |
| 4,573,986 A | 3/1986 | Minetola et al. |
| 4,578,072 A | 3/1986 | Lancaster |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A * | 9/1986 | Weisman .......... A61F 13/15203 604/368 |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,715,918 A | 12/1987 | Lang |
| 4,731,066 A | 3/1988 | Korpman |
| 4,731,070 A | 3/1988 | Koci |
| RE32,649 E | 4/1988 | Brandt et al. |
| 4,747,846 A | 5/1988 | Boland et al. |
| 4,764,325 A * | 8/1988 | Angstadt ............ A61F 13/15658 264/113 |
| 4,765,780 A * | 8/1988 | Angstadt ............ A61F 13/15658 264/113 |
| 4,773,905 A | 9/1988 | Molee |
| 4,784,892 A | 11/1988 | Storey et al. |

(56) References Cited

U.S. PATENT DOCUMENTS

| | | |
|---|---|---|
| 4,785,996 A | 11/1988 | Ziecker et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,808,178 A | 2/1989 | Aziz |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,904,440 A * | 2/1990 | Angstadt ............ A61F 13/15626 264/113 |
| 4,900,317 A | 3/1990 | Buell |
| 4,908,175 A * | 3/1990 | Angstadt ............ A61F 13/15585 264/113 |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Poiski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,085,654 A | 2/1992 | Buell |
| 5,087,255 A | 2/1992 | Sims et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,387,207 A | 2/1995 | Dyer et al. |
| 5,387,209 A | 2/1995 | Yamamoto et al. |
| 5,389,095 A | 2/1995 | Suzuki |
| 5,397,316 A | 3/1995 | Lavon et al. |
| 5,399,175 A | 3/1995 | Glaug et al. |
| 5,401,792 A | 3/1995 | Baku et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,462,541 A | 10/1995 | Bruemmer et al. |
| 5,476,458 A | 12/1995 | Glaug et al. |
| 5,486,166 A | 1/1996 | Bishop et al. |
| 5,490,846 A | 2/1996 | Ellis et al. |
| 5,492,962 A | 2/1996 | Lehrman et al. |
| 5,494,622 A | 2/1996 | Heath et al. |
| 5,499,978 A | 3/1996 | Buell et al. |
| 5,507,736 A | 4/1996 | Clear |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,560,878 A | 10/1996 | Dragoo et al. |
| 5,562,646 A | 10/1996 | Goldman et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,607,416 A | 5/1997 | Yamamoto et al. |
| 5,626,571 A | 5/1997 | Young et al. |
| 5,628,741 A | 5/1997 | Buell et al. |
| 5,635,191 A | 6/1997 | Roe |

(56) References Cited

U.S. PATENT DOCUMENTS

| | | |
|---|---|---|
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,674,215 A | 10/1997 | Ronnberg |
| 5,683,374 A | 11/1997 | Yamamoto |
| 5,685,874 A | 11/1997 | Buell et al. |
| 5,690,627 A | 11/1997 | Clear et al. |
| 5,691,035 A | 11/1997 | Chappell et al. |
| 5,691,036 A | 11/1997 | Chappell et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick-Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,855,572 A | 1/1999 | Schmidt |
| 5,858,013 A | 1/1999 | Kling |
| 5,865,823 A | 2/1999 | Curro |
| 5,865,824 A | 2/1999 | Chen |
| 5,866,173 A * | 2/1999 | Reiter ............... A61F 13/532 425/134 |
| 5,873,868 A | 2/1999 | Nakahata |
| 5,876,391 A | 3/1999 | Roe et al. |
| 5,891,118 A | 4/1999 | Toyoshima |
| 5,891,544 A | 4/1999 | Chappell et al. |
| 5,904,673 A | 5/1999 | Roe et al. |
| 5,927,052 A * | 7/1999 | Nippes ............... A23F 3/40 426/410 |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,033,199 A * | 3/2000 | Vonderhaar ....... A61F 13/15658 118/301 |
| 6,042,673 A | 3/2000 | Johnson et al. |
| 6,048,489 A * | 4/2000 | Reiter ............... A61F 13/532 264/113 |
| 6,050,984 A | 4/2000 | Fujioka et al. |
| 6,054,631 A | 4/2000 | Gent |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,258,996 B1 | 7/2001 | Goldman |
| 6,265,488 B1 | 7/2001 | Fujino et al. |
| 6,306,122 B1 | 10/2001 | Narawa et al. |
| 6,315,765 B1 | 11/2001 | Datta |
| 6,322,552 B1 | 11/2001 | Blenke et al. |
| 6,325,787 B1 | 12/2001 | Roe et al. |
| 6,326,525 B1 | 12/2001 | Hamajima |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,419,667 B1 | 7/2002 | Avalon et al. |
| 6,423,046 B1 | 7/2002 | Fujioka et al. |

(56) References Cited

U.S. PATENT DOCUMENTS

| | | |
|---|---|---|
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen et al. |
| 6,503,979 B1 | 1/2003 | Funk et al. |
| 6,506,186 B1 | 1/2003 | Roessler et al. |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen et al. |
| 6,521,812 B1 | 2/2003 | Graef |
| 6,524,294 B1 | 2/2003 | Hilston et al. |
| 6,525,240 B1 | 2/2003 | Graef |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LeMahieu et al. |
| 6,602,234 B2 | 8/2003 | Klemp et al. |
| 6,605,070 B2 | 8/2003 | Ludwig et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,652,798 B1 * | 11/2003 | Edvardsson ...... A61F 13/15658 |
| | | 264/112 |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B2 | 4/2004 | Johnson et al. |
| 6,734,335 B1 | 5/2004 | Graef |
| 6,790,798 B1 | 9/2004 | Suzuki et al. |
| 6,799,409 B2 * | 10/2004 | Altvater ............... A01J 21/02 |
| | | 53/122 |
| 6,805,174 B2 * | 10/2004 | Smith .................. B65B 1/366 |
| | | 141/103 |
| 6,809,158 B2 | 10/2004 | Ikeuchi et al. |
| 6,818,083 B2 | 11/2004 | Mcamish et al. |
| 6,830,800 B2 | 12/2004 | Curro et al. |
| 6,832,905 B2 * | 12/2004 | Delzer ............ A61F 13/15658 |
| | | 156/303 |
| 6,837,281 B2 * | 1/2005 | Spiers ................ B65B 1/366 |
| | | 141/125 |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 7,001,167 B2 | 2/2006 | Venturino |
| 7,014,632 B2 | 3/2006 | Takino et al. |
| 7,015,370 B2 | 3/2006 | Watanabe et al. |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita et al. |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,093,625 B2 * | 8/2006 | Smith .................. B65B 1/366 |
| | | 141/103 |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,250,481 B2 | 7/2007 | Jaworek et al. |
| 7,252,657 B2 | 8/2007 | Mishima |

(56) References Cited

U.S. PATENT DOCUMENTS

| | | | |
|---|---|---|---|
| 7,265,258 B2 | 9/2007 | Hamilton | |
| RE39,919 E | 11/2007 | Dodge, II et al. | |
| 7,311,968 B2 | 12/2007 | Ehrnsperger et al. | |
| 7,312,372 B2 | 12/2007 | Miyama | |
| 7,318,820 B2 | 1/2008 | LaVon et al. | |
| 7,329,244 B2 | 2/2008 | Otsubo | |
| 7,329,246 B2 | 2/2008 | Kinoshita | |
| 7,335,810 B2 | 2/2008 | Yoshimasa et al. | |
| 7,377,914 B2 | 5/2008 | LaVon | |
| 7,392,636 B2 * | 7/2008 | Conti | B65B 29/02 53/433 |
| 7,429,689 B2 | 9/2008 | Chen | |
| 7,435,244 B2 | 10/2008 | Schroer et al. | |
| 7,465,373 B2 | 12/2008 | Graef | |
| 7,500,969 B2 | 3/2009 | Mishima | |
| 7,504,552 B2 | 3/2009 | Tamura | |
| 7,521,109 B2 | 4/2009 | Suzuki et al. | |
| 7,521,587 B2 | 4/2009 | Busam et al. | |
| 7,537,832 B2 | 5/2009 | Carlucci et al. | |
| 7,547,815 B2 | 6/2009 | Ohashi | |
| 7,550,646 B2 | 6/2009 | Tamura | |
| 7,563,257 B2 | 7/2009 | Nakaiima | |
| 7,588,561 B2 | 9/2009 | Kenmochi | |
| 7,594,904 B2 | 9/2009 | Rosenfeld | |
| 7,625,363 B2 | 12/2009 | Yoshimasa | |
| 7,641,642 B2 | 1/2010 | Murai et al. | |
| 7,648,490 B2 | 1/2010 | Kuroda | |
| 7,652,111 B2 | 1/2010 | Hermeling et al. | |
| 7,661,248 B2 * | 2/2010 | Conti | B65B 1/366 222/218 |
| 7,666,173 B2 | 2/2010 | Mishima | |
| 7,666,174 B2 | 2/2010 | Kawakami et al. | |
| 7,687,596 B2 | 3/2010 | Hermeling et al. | |
| 7,695,461 B2 | 4/2010 | Rosenfeld | |
| 7,696,402 B2 | 4/2010 | Nishikawa | |
| 7,708,725 B2 | 5/2010 | Tamagawa | |
| 7,717,150 B2 | 5/2010 | Manabe | |
| 7,722,587 B2 | 5/2010 | Suzuki et al. | |
| 7,722,590 B2 | 5/2010 | Tsuji | |
| 7,727,217 B2 | 6/2010 | Hancock-Cooke | |
| 7,736,351 B2 | 6/2010 | Nigam | |
| 7,744,576 B2 | 6/2010 | Busam et al. | |
| 7,744,578 B2 | 6/2010 | Tanio et al. | |
| 7,750,203 B2 | 7/2010 | Busam et al. | |
| 7,754,822 B2 | 7/2010 | Daniel et al. | |
| 7,754,940 B2 | 7/2010 | Brisebois | |
| 7,759,540 B2 | 7/2010 | Litvay et al. | |
| 7,763,004 B2 | 7/2010 | Beck | |
| 7,767,875 B2 | 8/2010 | Olson | |
| 7,767,878 B2 | 8/2010 | Suzuki | |
| 7,772,420 B2 | 8/2010 | Hermeling et al. | |
| 7,786,341 B2 | 8/2010 | Schneider et al. | |
| 7,795,492 B2 | 9/2010 | Vartiainen | |
| 7,803,145 B2 | 9/2010 | Rosenfeld | |
| 7,849,889 B2 * | 12/2010 | Smith | B65B 1/366 141/125 |
| 7,850,672 B2 | 12/2010 | Guidotti et al. | |
| 7,851,667 B2 | 12/2010 | Becker et al. | |
| 7,855,314 B2 | 12/2010 | Hanao | |
| 7,857,797 B2 | 12/2010 | Kudo | |
| 7,858,842 B2 | 12/2010 | Komatsu | |
| 7,884,259 B2 | 2/2011 | Hanao | |
| 7,888,549 B2 | 2/2011 | Jansson et al. | |
| 7,906,065 B1 * | 3/2011 | Brown | A61F 13/15658 156/62.2 |
| 7,910,797 B2 | 3/2011 | Nandrea | |
| 7,935,207 B2 | 5/2011 | Zhao | |
| 7,935,861 B2 | 5/2011 | Suzuki | |
| 7,938,813 B2 | 5/2011 | Wang et al. | |
| 7,942,858 B2 | 5/2011 | Francoeur | |
| 7,951,126 B2 | 5/2011 | Nanjyo et al. | |
| 7,982,091 B2 | 7/2011 | Konawa | |
| 7,993,319 B2 | 8/2011 | Sperl | |
| 8,017,827 B2 | 9/2011 | Hundorf et al. | |
| 8,029,486 B2 | 10/2011 | Nakajima | |
| 8,034,991 B2 | 10/2011 | Bruzadin et al. | |
| 8,039,684 B2 | 10/2011 | Guidotti et al. | |
| 8,052,454 B2 | 11/2011 | Polnyi | |
| 8,109,915 B2 | 2/2012 | Shimoe | |
| 8,133,212 B2 | 3/2012 | Takada | |
| 8,148,598 B2 | 4/2012 | Tsang et al. | |
| 8,173,858 B2 | 5/2012 | Kuroda | |
| 8,178,747 B2 | 5/2012 | Venturino et al. | |
| 8,180,603 B2 * | 5/2012 | Blessing | A61F 13/15658 703/1 |
| 8,183,430 B2 | 5/2012 | Hakansson et al. | |
| 8,186,296 B2 | 5/2012 | Brown et al. | |
| 8,187,240 B2 | 5/2012 | Busam et al. | |
| 8,198,506 B2 | 6/2012 | Venturino et al. | |
| 8,211,815 B2 | 7/2012 | Baker | |
| 8,221,672 B2 * | 7/2012 | Brown | A61F 13/15658 156/62.2 |
| 8,236,715 B2 | 8/2012 | Schmidt et al. | |
| 8,237,012 B2 | 8/2012 | Miyama | |
| 8,246,594 B2 | 8/2012 | Sperl | |
| 8,258,367 B2 | 9/2012 | Lawson et al. | |
| 8,268,424 B1 | 9/2012 | Suzuki | |
| 8,273,943 B2 | 9/2012 | Noda | |
| 8,283,516 B2 | 10/2012 | Litvay | |
| 8,317,766 B2 | 11/2012 | Naoto | |
| 8,317,768 B2 | 11/2012 | Larsson | |
| 8,319,005 B2 | 11/2012 | Becker et al. | |
| 8,343,123 B2 | 1/2013 | Noda | |
| 8,361,047 B2 | 1/2013 | Mukai | |
| 8,364,451 B2 * | 1/2013 | Blessing | A61F 13/15658 703/1 |
| 8,377,025 B2 | 2/2013 | Nakajima | |
| 8,450,555 B2 | 5/2013 | Nhan et al. | |
| 8,496,637 B2 | 7/2013 | Hundorf et al. | |
| 8,519,213 B2 | 8/2013 | Venturino et al. | |
| 8,524,355 B2 | 9/2013 | Nakaoka | |
| 8,552,252 B2 | 10/2013 | Hundorf et al. | |
| 8,568,566 B2 | 10/2013 | Jackels et al. | |
| 8,581,019 B2 | 11/2013 | Carlucci et al. | |
| 8,590,582 B2 * | 11/2013 | Jackels | A61F 13/15658 141/12 |
| 8,603,058 B2 | 12/2013 | Sprerl et al. | |
| 8,604,270 B2 | 12/2013 | Venturino et al. | |
| 8,633,347 B2 | 1/2014 | Bianco et al. | |
| 8,674,170 B2 | 3/2014 | Busam et al. | |
| 8,766,031 B2 | 7/2014 | Becker et al. | |
| 8,772,570 B2 | 7/2014 | Kawakami et al. | |
| 8,785,715 B2 | 7/2014 | Wright et al. | |
| 8,791,318 B2 | 7/2014 | Becker et al. | |
| 8,986,474 B2 * | 3/2015 | Kufner | A61F 13/15634 156/167 |
| 9,340,363 B2 * | 5/2016 | Jackels | A61F 13/15658 |
| 2001/0007065 A1 | 7/2001 | Blanchard et al. | |
| 2001/0008964 A1 | 7/2001 | Kurata et al. | |
| 2001/0020157 A1 | 9/2001 | Mizutani | |
| 2001/0037101 A1 | 11/2001 | Allan et al. | |
| 2001/0044610 A1 | 11/2001 | Kim | |
| 2002/0007167 A1 | 1/2002 | Dan | |
| 2002/0007169 A1 | 1/2002 | Graef et al. | |
| 2002/0016122 A1 | 2/2002 | Curro et al. | |
| 2002/0016579 A1 | 2/2002 | Stenberg | |
| 2002/0045881 A1 | 4/2002 | Kusibojoska et al. | |
| 2002/0062112 A1 | 5/2002 | Mizutani | |
| 2002/0062116 A1 | 5/2002 | Mizutani et al. | |
| 2002/0065498 A1 | 5/2002 | Ohashi | |
| 2002/0072471 A1 | 6/2002 | Ikeuchi et al. | |
| 2002/0082575 A1 | 6/2002 | Dan | |
| 2002/0087139 A1 | 7/2002 | Popp et al. | |
| 2002/0102392 A1 | 8/2002 | Fish et al. | |
| 2002/0123728 A1 | 9/2002 | Graef et al. | |
| 2002/0151634 A1 | 10/2002 | Rohrbaugh et al. | |
| 2002/0151861 A1 | 10/2002 | Klemp et al. | |
| 2002/0173211 A1 | 11/2002 | Popp et al. | |
| 2002/0192366 A1 | 12/2002 | Cramer et al. | |
| 2003/0034085 A1 * | 2/2003 | Spiers | B65B 1/366 141/125 |
| 2003/0036741 A1 | 2/2003 | Abba et al. | |
| 2003/0078553 A1 | 4/2003 | Wada | |
| 2003/0088223 A1 | 5/2003 | Vogt et al. | |

(56) References Cited

U.S. PATENT DOCUMENTS

| | | |
|---|---|---|
| 2003/0105190 A1 | 6/2003 | Diehl et al. |
| 2003/0114816 A1 | 6/2003 | Underhill |
| 2003/0114818 A1 | 6/2003 | Benecke et al. |
| 2003/0120235 A1 | 6/2003 | Boulanger |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0143324 A1* | 7/2003 | Delzer .............. A61F 13/15772 427/180 |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0236512 A1 | 12/2003 | Baker |
| 2004/0019338 A1 | 1/2004 | Litvay et al. |
| 2004/0020554 A1* | 2/2004 | Smith .................... B65B 1/366 141/67 |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0096623 A1 | 5/2005 | Nhan et al. |
| 2005/0137543 A1 | 6/2005 | Underhill et al. |
| 2005/0148258 A1 | 7/2005 | Chakravarty |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0229543 A1 | 10/2005 | Tippey |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0004335 A1 | 1/2006 | Wang et al. |
| 2006/0005919 A1 | 1/2006 | Schewe et al. |
| 2006/0021695 A1 | 2/2006 | Blessing et al. |
| 2006/0024433 A1 | 2/2006 | Blessing et al. |
| 2006/0048880 A1* | 3/2006 | Blessing ........... A61F 13/15658 156/60 |
| 2006/0073969 A1 | 4/2006 | Torli et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2007/0027436 A1 | 2/2007 | Nakagawa et al. |
| 2007/0032770 A1 | 2/2007 | LaVon et al. |
| 2007/0043191 A1 | 2/2007 | Hermeling et al. |
| 2007/0043330 A1 | 2/2007 | Lankhof et al. |
| 2007/0073253 A1 | 3/2007 | Miyama et al. |
| 2007/0078422 A1 | 4/2007 | Glaug et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0093768 A1 | 4/2007 | Roe et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0197987 A1 | 8/2007 | Tsang et al. |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0282288 A1 | 12/2007 | Noda |
| 2007/0282290 A1 | 12/2007 | Cole |
| 2007/0282291 A1 | 12/2007 | Cole |
| 2007/0284012 A1* | 12/2007 | Smith ................ A24D 3/0225 141/1 |
| 2008/0027402 A1 | 1/2008 | Schmidt et al. |
| 2008/0032035 A1 | 2/2008 | Schmidt et al. |
| 2008/0091159 A1 | 4/2008 | Carlucci |
| 2008/0119810 A1 | 5/2008 | Kuroda |
| 2008/0125735 A1 | 5/2008 | Busam et al. |
| 2008/0215166 A1* | 9/2008 | Blessing ........... A61F 13/15658 700/31 |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0281287 A1 | 11/2008 | Marcelo |
| 2008/0294140 A1 | 11/2008 | Ecker et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0062760 A1 | 3/2009 | Wright et al. |
| 2009/0112173 A1 | 4/2009 | Bissah |
| 2009/0112175 A1 | 4/2009 | Bissah et al. |

(56) References Cited

U.S. PATENT DOCUMENTS

| | | |
|---|---|---|
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241097 A1 | 9/2010 | Nigam et al. |
| 2010/0262099 A1 | 10/2010 | Klofta |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2010/0331801 A1 | 12/2010 | Kawakami et al. |
| 2011/0041999 A1* | 2/2011 | Hundorf ............ A61F 13/15658 156/276 |
| 2011/0042844 A1* | 2/2011 | Brown ............... A61F 13/15658 264/101 |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan |
| 2011/0125120 A1 | 5/2011 | Nishitani |
| 2011/0130732 A1* | 6/2011 | Jackels ............. A61F 13/15658 604/365 |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda et al. |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0203715 A1* | 8/2011 | Brown ............... A61F 13/15658 156/62.2 |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0319846 A1 | 12/2011 | Rinnert et al. |
| 2011/0319848 A1 | 12/2011 | McKiernan et al. |
| 2011/0319851 A1 | 12/2011 | Kudo |
| 2012/0004633 A1 | 1/2012 | Marcelo |
| 2012/0016326 A1 | 1/2012 | Brennan et al. |
| 2012/0022479 A1 | 1/2012 | Cotton |
| 2012/0024470 A1* | 2/2012 | Hundorf ............ A61F 13/15658 156/250 |
| 2012/0035566 A1 | 2/2012 | Sagisaka |
| 2012/0035576 A1 | 2/2012 | Ichikawa |
| 2012/0056347 A1* | 3/2012 | Taniguchi ......... A61F 13/15658 264/101 |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0165776 A1 | 6/2012 | Rinnert et al. |
| 2012/0175056 A1 | 7/2012 | Tsang |
| 2012/0184934 A1 | 7/2012 | Venturino |
| 2012/0203527 A1* | 8/2012 | Blessing ........... A61F 13/15658 703/2 |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0270715 A1 | 10/2012 | Motegi et al. |
| 2012/0271262 A1 | 10/2012 | Venturino |
| 2012/0282364 A1* | 11/2012 | Brown .............. A61F 13/15658 425/224 |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau et al. |
| 2013/0174959 A1* | 7/2013 | Kufner ............. A61F 13/15634 156/62.2 |
| 2013/0211354 A1 | 8/2013 | Tsuji et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0069779 A1* | 3/2014 | Jackels ............. A61F 13/15658 198/703 |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0324007 A1 | 10/2014 | Hundorf et al. |
| 2014/0324008 A1 | 10/2014 | Hundorf et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 197 54 684 A1 | 6/1999 |
| DE | 10204937 A1 | 8/2003 |
| EP | 083022 | 7/1983 |
| EP | 149880 | 7/1985 |
| EP | 0149880 A2 | 7/1985 |
| EP | 0203289 A2 | 12/1986 |
| EP | 0206208 | 12/1986 |
| EP | 209561 B1 | 1/1987 |

(56) References Cited

FOREIGN PATENT DOCUMENTS

| | | |
|---|---|---|
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 863733 | 9/1998 |
| EP | 971751 | 9/1998 |
| EP | 875224 A1 | 11/1998 |
| EP | 880955 | 12/1998 |
| EP | 891758 | 1/1999 |
| EP | 0893115 | 1/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953324 | 11/1999 |
| EP | 953326 | 11/1999 |
| EP | 0978263 A1 | 2/2000 |
| EP | 985397 B1 | 3/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 1116479 A2 | 7/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1262531 A1 | 12/2002 |
| EP | 1263374 B1 | 12/2002 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621167 | 2/2006 |
| EP | 1632206 | 3/2006 |
| EP | 1642556 | 4/2006 |
| EP | 1656162 | 5/2006 |
| EP | 1669046 | 6/2006 |
| EP | 1688114 | 8/2006 |
| EP | 2314265 | 8/2006 |
| EP | 1700586 | 9/2006 |
| EP | 1723939 | 11/2006 |
| EP | 1738727 | 1/2007 |
| EP | 1754461 | 2/2007 |
| EP | 1774940 | 4/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 2444046 | 4/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 55-72928 U | 5/1980 |

(56) References Cited

FOREIGN PATENT DOCUMENTS

| | | |
|---|---|---|
| JP | 59-8322 U | 1/1984 |
| JP | 63-0148323 U | 9/1988 |
| JP | 03-224481 B2 | 10/1991 |
| JP | 04-122256 | 4/1992 |
| JP | 06-269475 A | 9/1994 |
| JP | 10-328232 | 12/1998 |
| JP | 11-033056 A | 2/1999 |
| JP | 11-318980 | 11/1999 |
| JP | 2000-232985 | 8/2000 |
| JP | 2000-238161 | 9/2000 |
| JP | 2001-037810 | 2/2001 |
| JP | 2001-046435 A | 2/2001 |
| JP | 2001-120597 | 5/2001 |
| JP | 2001-158074 | 6/2001 |
| JP | 2001-171029 A | 6/2001 |
| JP | 2001-178768 A | 7/2001 |
| JP | 2001-198157 | 7/2001 |
| JP | 2001-224626 A | 8/2001 |
| JP | 03-420481 B2 | 11/2001 |
| JP | 2001-353174 A | 12/2001 |
| JP | 2002-052042 A | 2/2002 |
| JP | 2002-113800 A | 4/2002 |
| JP | 2002-165832 | 6/2002 |
| JP | 2002-165836 | 6/2002 |
| JP | 2002-272769 A | 9/2002 |
| JP | 2002-325792 A | 11/2002 |
| JP | 2002-325799 A | 11/2002 |
| JP | 2002-369841 A | 12/2002 |
| JP | 2003-153955 A | 5/2003 |
| JP | 2003-265524 A | 9/2003 |
| JP | 2003-275237 | 9/2003 |
| JP | 2004-089269 | 3/2004 |
| JP | 03-566012 B2 | 6/2004 |
| JP | 03-568146 B2 | 6/2004 |
| JP | 03-616077 B2 | 11/2004 |
| JP | 2004-337314 A | 12/2004 |
| JP | 2004-337385 A | 12/2004 |
| JP | 03-640475 B2 | 1/2005 |
| JP | 2005-000312 A | 1/2005 |
| JP | 03-660816 B2 | 3/2005 |
| JP | 03-676219 B2 | 5/2005 |
| JP | 03-688403 B2 | 6/2005 |
| JP | 03-705943 B2 | 8/2005 |
| JP | 03-719819 B2 | 9/2005 |
| JP | 03-724963 B2 | 9/2005 |
| JP | 03-725008 B2 | 9/2005 |
| JP | 03-737376 B2 | 11/2005 |
| JP | 2006-014792 A | 1/2006 |
| JP | 03-781617 B2 | 3/2006 |
| JP | 2006-110329 | 4/2006 |
| JP | 03-801449 B2 | 5/2006 |
| JP | 2006-116036 A | 5/2006 |
| JP | 03-850102 B2 | 9/2006 |
| JP | 03-850207 B2 | 9/2006 |
| JP | 03-856941 B2 | 9/2006 |
| JP | 03-868628 B2 | 10/2006 |
| JP | 03-874499 B2 | 11/2006 |
| JP | 03-877702 B2 | 11/2006 |
| JP | 2006-325639 A | 12/2006 |
| JP | 2006-346021 | 12/2006 |
| JP | 03-904356 B2 | 1/2007 |
| JP | 2007-007455 A | 1/2007 |
| JP | 2007-007456 A | 1/2007 |
| JP | 03-926042 B2 | 3/2007 |
| JP | 03-934855 B2 | 3/2007 |
| JP | 2007-089906 A | 4/2007 |
| JP | 2007-105198 A | 4/2007 |
| JP | 2007-152033 A | 6/2007 |
| JP | 03-986210 B2 | 7/2007 |
| JP | 03-986222 B2 | 7/2007 |
| JP | 2007-167453 | 7/2007 |
| JP | 2007-175515 A | 7/2007 |
| JP | 2007-195665 A | 8/2007 |
| JP | 2007-267763 A | 10/2007 |
| JP | 2007-275491 A | 10/2007 |
| JP | 04-035341 B2 | 11/2007 |
| JP | 04-058281 B2 | 12/2007 |
| JP | 04-061086 B2 | 12/2007 |
| JP | 04-092319 B2 | 3/2008 |
| JP | 2008-080150 A | 4/2008 |
| JP | 2008-093289 A | 4/2008 |
| JP | 04-124322 B2 | 5/2008 |
| JP | 2008-119081 A | 5/2008 |
| JP | 2008-136739 A | 6/2008 |
| JP | 2008-136877 A | 6/2008 |
| JP | 04-148594 B2 | 7/2008 |
| JP | 04-148620 B2 | 7/2008 |
| JP | 2008-154606 A | 7/2008 |
| JP | 04-162609 B2 | 8/2008 |
| JP | 04-162637 B2 | 8/2008 |
| JP | 04-166923 B2 | 8/2008 |
| JP | 04-167406 B2 | 8/2008 |
| JP | 04-173723 B2 | 8/2008 |
| JP | 04-190675 B2 | 9/2008 |
| JP | 04-190693 B2 | 9/2008 |
| JP | 04-208338 B2 | 10/2008 |
| JP | 2008-246089 | 10/2008 |
| JP | 04-230971 B2 | 12/2008 |
| JP | 2008-295475 A | 12/2008 |
| JP | 2008-295713 A | 12/2008 |
| JP | 04-261593 B2 | 2/2009 |
| JP | 2009-112590 | 5/2009 |
| JP | 04-322228 B2 | 6/2009 |
| JP | 2009-136601 | 6/2009 |
| JP | 2009-142401 A | 7/2009 |
| JP | 2009-201878 A | 9/2009 |
| JP | 04-392936 B2 | 10/2009 |
| JP | 2009-232987 A | 10/2009 |
| JP | 2009-261777 A | 11/2009 |
| JP | 2009-291473 A | 12/2009 |
| JP | 2009-297048 A | 12/2009 |
| JP | 04-458702 B2 | 2/2010 |
| JP | 04-459013 B2 | 2/2010 |
| JP | 2010-022560 | 2/2010 |
| JP | 04-481325 B2 | 3/2010 |
| JP | 2010-051654 A | 3/2010 |
| JP | 2010-063814 A | 3/2010 |
| JP | 2010-063944 A | 3/2010 |
| JP | 04-492957 B2 | 4/2010 |
| JP | 2010-068954 A | 4/2010 |
| JP | 2010-075462 A | 4/2010 |
| JP | 2010-082059 A | 4/2010 |
| JP | 2010-104545 A | 5/2010 |
| JP | 2010-104547 A | 5/2010 |
| JP | 2010-110535 A | 5/2010 |
| JP | 2010-119454 A | 6/2010 |
| JP | 2010-119605 A | 6/2010 |
| JP | 2010-119743 A | 6/2010 |
| JP | 2010-131131 A | 6/2010 |
| JP | 2010-131132 A | 6/2010 |
| JP | 2010-131206 | 6/2010 |
| JP | 2010-131297 A | 6/2010 |
| JP | 2010-136917 A | 6/2010 |
| JP | 2010-136973 A | 6/2010 |
| JP | 04-540563 B2 | 7/2010 |
| JP | 04-587947 B2 | 9/2010 |
| JP | 2010-194124 A | 9/2010 |
| JP | 2010-201093 | 9/2010 |
| JP | 2010-221067 | 10/2010 |
| JP | 04-620299 B2 | 11/2010 |
| JP | 04-627472 B2 | 11/2010 |
| JP | 04-627473 B2 | 11/2010 |
| JP | 04-638087 B2 | 12/2010 |
| JP | 04-652626 B2 | 12/2010 |
| JP | 2010-273842 A | 12/2010 |
| JP | 2010-284418 A | 12/2010 |
| JP | 2010-284418 A | 12/2010 |
| JP | 2011-000480 A | 1/2011 |
| JP | 2011-030700 | 2/2011 |
| JP | 04-693574 B2 | 3/2011 |
| JP | 2011-067484 A | 4/2011 |
| JP | 2011-072720 A | 4/2011 |
| JP | 2011-104014 | 6/2011 |
| JP | 2011-104122 A | 6/2011 |

(56) References Cited

FOREIGN PATENT DOCUMENTS

| | | |
|---|---|---|
| JP | 2011-120661 A | 6/2011 |
| JP | 2011-125360 A | 6/2011 |
| JP | 2011-125537 | 6/2011 |
| JP | 04-776516 B2 | 7/2011 |
| JP | 2011-130797 A | 7/2011 |
| JP | 2011-130799 A | 7/2011 |
| JP | 2011-156032 A | 8/2011 |
| JP | 2011-156070 A | 8/2011 |
| JP | 2011-156254 | 8/2011 |
| JP | 04-824882 B2 | 9/2011 |
| JP | 48-50272 B2 | 10/2011 |
| JP | 04-855533 B2 | 11/2011 |
| JP | 2011-239858 | 12/2011 |
| JP | 04-931572 B2 | 2/2012 |
| JP | 04-937225 B2 | 3/2012 |
| JP | 04-953618 B2 | 3/2012 |
| JP | 04-969437 B2 | 4/2012 |
| JP | 04-969640 B2 | 4/2012 |
| JP | 04-974524 B2 | 4/2012 |
| JP | 04-979780 B2 | 4/2012 |
| JP | 49-71491 B2 | 4/2012 |
| JP | 05-016020 B2 | 6/2012 |
| JP | 05-027364 B2 | 6/2012 |
| JP | 05-031082 B2 | 7/2012 |
| JP | 05-042351 B2 | 7/2012 |
| JP | 05-043569 B2 | 7/2012 |
| JP | 05-043591 B2 | 7/2012 |
| JP | 05-046488 B2 | 7/2012 |
| JP | 2012-125625 A | 7/2012 |
| JP | 05-053765 B2 | 8/2012 |
| JP | 05-070275 B2 | 8/2012 |
| JP | 05-079931 B1 | 9/2012 |
| JP | 05-080189 B2 | 9/2012 |
| JP | 05-084442 B2 | 9/2012 |
| JP | 05-084476 B2 | 9/2012 |
| JP | 05-089269 B2 | 9/2012 |
| JP | 50-85770 B2 | 9/2012 |
| JP | 05-113146 B2 | 10/2012 |
| JP | 05-129536 B2 | 11/2012 |
| JP | 05-105884 B2 | 12/2012 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO90/15830 | 12/1990 |
| WO | WO93/21237 | 10/1993 |
| WO | WO93/21879 | 11/1993 |
| WO | WO95/10996 | 4/1995 |
| WO | WO95/11652 | 5/1995 |
| WO | WO95/14453 | 6/1995 |
| WO | WO95/15139 | 6/1995 |
| WO | WO95/16424 | 6/1995 |
| WO | WO95/16746 | 6/1995 |
| WO | WO95/19753 | 7/1995 |
| WO | WO95/21596 | 8/1995 |
| WO | WO95/24173 | 9/1995 |
| WO | WO95/29657 | 11/1995 |
| WO | WO95/32698 | 12/1995 |
| WO | WO95/34329 | 12/1995 |
| WO | WO96/16624 | 6/1996 |
| WO | WO96/19173 | 6/1996 |
| WO | WO97/11659 | 4/1997 |
| WO | WO97/17922 | 5/1997 |
| WO | WO98/16179 | 4/1998 |
| WO | WO98/16180 | 4/1998 |
| WO | WO98/43684 | 10/1998 |
| WO | WO99/13813 | 3/1999 |
| WO | WO99/34841 | 7/1999 |
| WO | WO99/51178 | 10/1999 |
| WO | WO2000/000235 | 1/2000 |
| WO | WO2000/032145 | 6/2000 |
| WO | WO2000/059430 | 10/2000 |
| WO | WO2001/015647 | 3/2001 |
| WO | WO2001/026596 | 4/2001 |
| WO | WO2002/007663 | 1/2002 |
| WO | WO2002/032962 | 4/2002 |
| WO | WO2002/064877 | 8/2002 |
| WO | WO2002/067809 | 9/2002 |
| WO | WO2003/009794 | 2/2003 |
| WO | WO2003/053297 | 7/2003 |
| WO | WO2003/105738 | 12/2003 |
| WO | WO2004/021946 | 3/2004 |
| WO | WO2004/049995 | 6/2004 |
| WO | WO2004/071539 | 8/2004 |
| WO | WO2004/084784 | 10/2004 |
| WO | WO2004/105664 | 12/2004 |
| WO | WO2005/018694 | 3/2005 |
| WO | WO2005/087164 | 9/2005 |
| WO | WO2006/104024 | 5/2006 |
| WO | WO2006/059922 | 6/2006 |
| WO | WO2006/062258 | 6/2006 |
| WO | WO2006/066029 | 6/2006 |
| WO | WO2006/083584 | 8/2006 |
| WO | WO2006/134904 | 12/2006 |
| WO | WO2006/134906 | 12/2006 |
| WO | WO2007/000315 | 1/2007 |
| WO | WO2007/046052 | 4/2007 |
| WO | WO2007/047598 | 4/2007 |
| WO | WO2007/049725 | 5/2007 |
| WO | WO2007/061035 | 5/2007 |
| WO | WO2007/142145 | 12/2007 |
| WO | WO2007/148502 | 12/2007 |
| WO | WO2008/018922 | 2/2008 |
| WO | WO2008/065945 | 6/2008 |
| WO | WO2008/146749 | 12/2008 |
| WO | WO2008/155699 | 12/2008 |
| WO | WO2009/004941 | 1/2009 |
| WO | WO2009/005431 | 1/2009 |
| WO | WO2009/139248 | 1/2009 |
| WO | WO2009/139255 | 1/2009 |
| WO | WO2009/041223 | 4/2009 |
| WO | WO2009/096108 | 8/2009 |
| WO | WO2009/107435 | 9/2009 |
| WO | WO2009/122830 | 10/2009 |
| WO | WO2009/155264 | 12/2009 |
| WO | WO2009/155265 | 12/2009 |
| WO | WO2010/071508 | 6/2010 |
| WO | WO2010/074319 | 7/2010 |
| WO | WO2010/107096 | 9/2010 |
| WO | WO2010/114052 | 10/2010 |
| WO | WO2010/117015 | 10/2010 |
| WO | WO2011/053044 | 5/2011 |
| WO | WO2011/118725 | 9/2011 |
| WO | WO2011/118842 | 9/2011 |
| WO | WO2011/145653 | 11/2011 |
| WO | WO2011/150955 | 12/2011 |
| WO | WO2011/163582 | 12/2011 |
| WO | WO2012/002252 | 1/2012 |
| WO | WO2012/014436 | 2/2012 |
| WO | WO2012/042908 | 4/2012 |
| WO | WO2012/043077 | 4/2012 |
| WO | WO2012/043078 | 4/2012 |
| WO | WO2012/052172 | 4/2012 |
| WO | WO2012/043082 | 5/2012 |
| WO | WO2012/067216 | 5/2012 |
| WO | WO2012/073499 | 6/2012 |
| WO | WO2012/090508 | 7/2012 |
| WO | WO2012/91016 | 7/2012 |
| WO | WO2012/101934 | 8/2012 |
| WO | WO2012/102034 | 8/2012 |
| WO | WO2012/117824 | 9/2012 |
| WO | WO2012/132460 | 10/2012 |
| WO | WO2012/170778 | 12/2012 |
| WO | WO2012/170779 | 12/2012 |
| WO | WO2012/170781 | 12/2012 |
| WO | WO2012/170808 | 12/2012 |
| WO | WO2012/174026 | 12/2012 |
| WO | WO2013/001788 | 1/2013 |

(56) References Cited

FOREIGN PATENT DOCUMENTS

| WO | WO2013/060733 | 5/2013 |
| WO | WO2014/078247 | 5/2014 |

OTHER PUBLICATIONS

International Search Report, PCT/US2010/058259, dated Feb. 16, 2011, 7 pages.
All Office Actions, U.S. Appl. No. 12/958,484.
All Office Actions, U.S. Appl. No. 14/077,487.

* cited by examiner

US 10,004,647 B2

APPARATUS AND METHOD FOR TRANSFERRING PARTICULATE MATERIAL

FIELD OF THE INVENTION

This invention relates to an apparatus for transferring, at high speed and in a very effective and accurate manner, particulate material from a feeder into reservoirs of a moving endless surface, e.g. a drum, by use of a pressure/guiding means, e.g. a specific three-dimensional plate, for applying pressure onto said particulate material present between said plate and said moving endless surface, and guiding said particulate material into said reservoirs, and then transferring the particulate material with said moving endless surface with reservoirs to a substrate; the apparatus and method being in particular useful for the production of absorbent structures for absorbent articles.

BACKGROUND TO THE INVENTION

Traditionally, absorbent articles such as diapers comprise an absorbent core with water-absorbent (cellulose) fibers and particles of superabsorbent polymer particle, also referred to as particles of absorbent gelling material ("AGM"), enclosed by a substrate material, or supported by a substrate material and then closed by a further material, e.g. such as a nonwoven.

Absorbent articles with so-called profiled absorbent cores have been developed, whereby certain regions of the article comprise more AGM than other regions. In such instances, accurate deposition of AGM is important to obtain the required profile. Furthermore, in the case of absorbent cores with only small amounts of, or no, cellulose fibers (having thus AGM particles as the only liquid storage material) accurate AGM distribution is highly important.

Various approaches have been proposed for obtaining absorbent cores with primarily AGM particles and for obtaining absorbent cores that have AGM particles in a specific profile or distribution, such as a predetermined pattern, thickness profile, or adjusting various components of the manufacturing apparatus that act in the machine direction ("MD"), or cross-direction ("CD"). These approaches include indirect printing methods, whereby the AGM particles are taken up by a drum from a bulk storage of AGM particles—said roll or drum having reservoirs on the surface thereof, the number, size and position of which determining the amount and pattern of AGM granules taken up by the drum- and whereby the drum then rotates towards a substrate such as a nonwoven, to then release the AGM onto the substrate (carried by a moving surface).

Surprisingly, the inventors found that such proposed indirect printing processes are in some instances difficult to run at high speed, for example at speeds of more than 800 ppm or more than 1000 ppm (parts (absorbent cores) per minute), in particular when fine particulate material is used and/or when small (and large quantities of) reservoirs are used. It has been found that at high speeds, the AGM particles are not always satisfactorily dropped (e.g. from a feeder/hopper) into the reservoirs of the roll/drum. Reservoirs may only be partially filled, whilst at certain areas of the drum excess AGM may build up. If vacuum (in the roll/drum) is used to aid filling of the reservoirs, then this AGM build-up may obstruct the vacuum suction and this it may further obstruct the filling of the reservoirs This thus may result in an inaccurate distribution of the AGM in the absorbent cores, or even defects in the formed absorbent cores.

The inventors have now found an improved apparatus and method for producing, even at high speed, (absorbent) structures comprising particulate (absorbent) material; said apparatus and method are furthermore able to employ a moving surface (e.g. roll or drum) with a large number of small reservoirs, whilst still delivering accurate filling.

SUMMARY OF THE INVENTION

Aspects of the invention provide an apparatus (1), and method using such apparatus, that includes a particulate material feeder (30) for feeding particulate material to a first moving endless surface (40) (e.g. drum) with reservoirs (50), adjacent to said feeder, and including a means (e.g. three dimensional plate (10)) for guiding said particulate material and applying first and subsequent second pressures on part of said particulate material (100), said first pressure substantially perpendicular to the process direction and subsequently said second pressure being non-perpendicular to the process direction, as described herein, to guide said material into said reservoirs (50); said means or plate (10) being typically connected to a pressure control means.

In a first embodiment the invention relates to an apparatus (1) for making a structure that comprises particulate material (100) supported or enclosed by a substrate material (110), including:

a) a particulate material feeder (30) for feeding particulate material (100) to:
b) a first moving endless surface (40) with a direction of movement (MD) (per surface area of said surface) and with a plurality of reservoirs (50), said surface (40) being adjacent said feeder (30), said first moving endless surface (40) and reservoirs (50) thereof being for receiving said particulate material (100) from said first particulate material feeder (30) and for transferring it directly or indirectly to:
c) a second moving endless surface (200), being said substrate material (110) or being a moving endless surface carrying said substrate material (110), for receiving said particulate material (100) directly or indirectly from said first moving endless surface (40); and
d) a three-dimensional plate (10), for applying pressure on part of said particulate material (100) and for guiding said particulate material (100) into said reservoirs (50), said plate (10) being positioned adjacent said feeder (30) and adjacent said first moving endless surface (40), said plate (10) having a first plate face adjacent said first moving endless surface (40), said plate face having at least:
   i) a first surface area (11) substantially parallel to said first moving endless surface (40), said first area being for (and capable of) applying pressure on said part of said particulate material (100) when present between said first surface area (11) and said first moving endless surface (40);
   ii) a second surface area (12) neighboring said first surface area (11), positioned downstream from the first surface area (11) (in MD), said second surface area (12) being non-parallel to said first moving endless surface (40) and leading from said first surface area (11) towards said first moving endless surface (40), said first surface area (11) and said second surface area (12) are connected to one another, preferably under an angle, including a rounded angle (e.g. curvature, as described herein) or straight angle, and/or said second surface area (12)

preferably having an average angle with said first moving endless surface (40) of between 10° and 80°.

In some embodiments herein the plate face has a third surface area (13), neighboring said second surface area (12), being downstream from said second surface area (12)(in MD), said third surface area (13) being substantially parallel to said first moving endless surface (40) and in closer proximity thereto than said first surface area (11).

The invention also relates to a method for making a structure that comprises particulate material (100) supported or enclosed by a substrate material (110), including the steps of
- a) feeding a first particulate material (100) with a feeder (30) to a first moving endless surface (40) with a plurality of reservoirs (50), adjacent said feeder (30);
- b) allowing flow of said particulate material (100), or part thereof, into a volume space present between said first moving endless surface (40) and a three-dimensional plate (10), adjacent said feeder (30) and adjacent and opposing said first moving endless surface (40); and contacting a part of said particulate material (100) with said three dimensional plate (10), said plate having a first plate face adjacent said first moving endless surface (40), and said plate face having:
  - i) a first surface area (11) substantially parallel to said first moving endless surface (40); and;
  - ii) a second surface area (12) neighboring said first surface area (11), being downstream (in MD) from said first surface area (11), said second surface area (12) being non-parallel to said first moving endless surface (40) and leading from said first surface area (11) towards said first moving endless surface (40), said first surface area (11) and said second surface area (12) are connected to one another, e.g. under an angle, including a rounded angle (i.e. curvature) or a straight angle; preferably said second surface area (12) having an average angle with said first moving endless surface (40) of between 10° and 80°.
- c) applying a pressure with said plate onto at least a portion of said particulate material (100) present between said first plate face and said first moving endless surface (40), guiding (or optionally forcing or pressurizing or pushing), said material into said reservoirs (50);
- d) transferring said particulate material (100) in said reservoirs (50) of said first moving endless surface (40) directly or indirectly to a second moving endless surface (200), being, or carrying, said substrate material (110);
- e) depositing said particulate material (100) onto said substrate material (110).

Each of said first and second surface area have, in some embodiments, an (average) length dimension (in MD) of at least 2 mm; and/or a certain length in MD relative to the distance between centre points of neighbouring reservoirs, as described below.

Said pressure application step c) includes, in some embodiments herein, preferably: firstly applying a pressure, with said first surface area (11) of said plate (10), said pressure being substantially perpendicular to the direction of movement of the first moving endless surface (MD), thereby guiding, or optionally pushing, at least a first portion of said particulate material (100) into said reservoirs (50); and secondly, applying a pressure with said plate face's second surface area (12)s aid pressure being non-perpendicular to the direction of movement of the first moving endless surface (MD), thereby guiding, or optionally pushing, at least a second portion of said particulate material (100) into said reservoirs (50).

The first moving endless surface (40) has for example a surface speed of at least 4.5 m/s, or at least 6.0 m/s, or at least 7.0 m/s, or at least 9.0 m/s.

Said particulate material (100) may have for example a mass median particle size of from 150, or from 200 microns, to 1000 or to 900 microns, or from 300, to 800 or to 700 microns. It may be particulate absorbent polymeric material, as described herein.

The reservoirs (50) may for example have a maximum depth (perpendicular to MD) of from 1.0 to 8.0 mm, or from 1.5 mm to 5.0 mm or to 3.0 mm (herein referred to as average maximum depth: maximum per reservoir, and averaged overall all reservoirs (50), as further described below). The reservoirs (50) may for example have an average maximum dimension (e.g. diameter) in MD (averaged over all reservoirs (50), maximum per reservoir) of up to 20 mm, or up to 10 mm, or up to 6 mm.

In a further embodiment herein, the invention provides an apparatus (1) for making a structure that comprises particulate material (100) supported or enclosed by a substrate material (110), including:
- a) a particulate material feeder (30), said feeder (30) being for feeding particulate material (100) to:
- b) a first moving endless surface (40) with a direction of movement (MD) (per surface area of said surface, as defined herein) and with a plurality of reservoirs (50), said surface (40) being adjacent said feeder (30), said first moving endless surface (40) and reservoirs (50) thereof being for receiving said particulate material (100) from said first particulate material (100)
- c) a second moving endless surface (200), being said substrate material (110) or being a moving endless surface carrying said substrate material (110), for receiving said particulate material (100) directly or indirectly from said first moving endless surface (40); and
- d) a first pressure means being positioned adjacent said first moving endless surface (40), for applying pressure on at least part of said particulate material (100) and optionally on part of said first moving endless surface (40), said pressure being in a direction substantially perpendicular to the direction of movement of said moving endless surface (MD) (per surface area where said pressure is applied);
- e) a second pressure means adjacent said first moving endless surface (40) and adjacent said first pressure means, for applying pressure on at least part of said particulate material (100), said pressure (in an area) being in a direction non-perpendicular to the direction of movement of said moving endless surface (MD) in said area.

The invention also provides absorbent structures obtainable by the method or with the apparatus (1) of the invention, as described herein.

DETAILED DESCRIPTION OF THE INVENTION

Particulate Material

Figure 1:
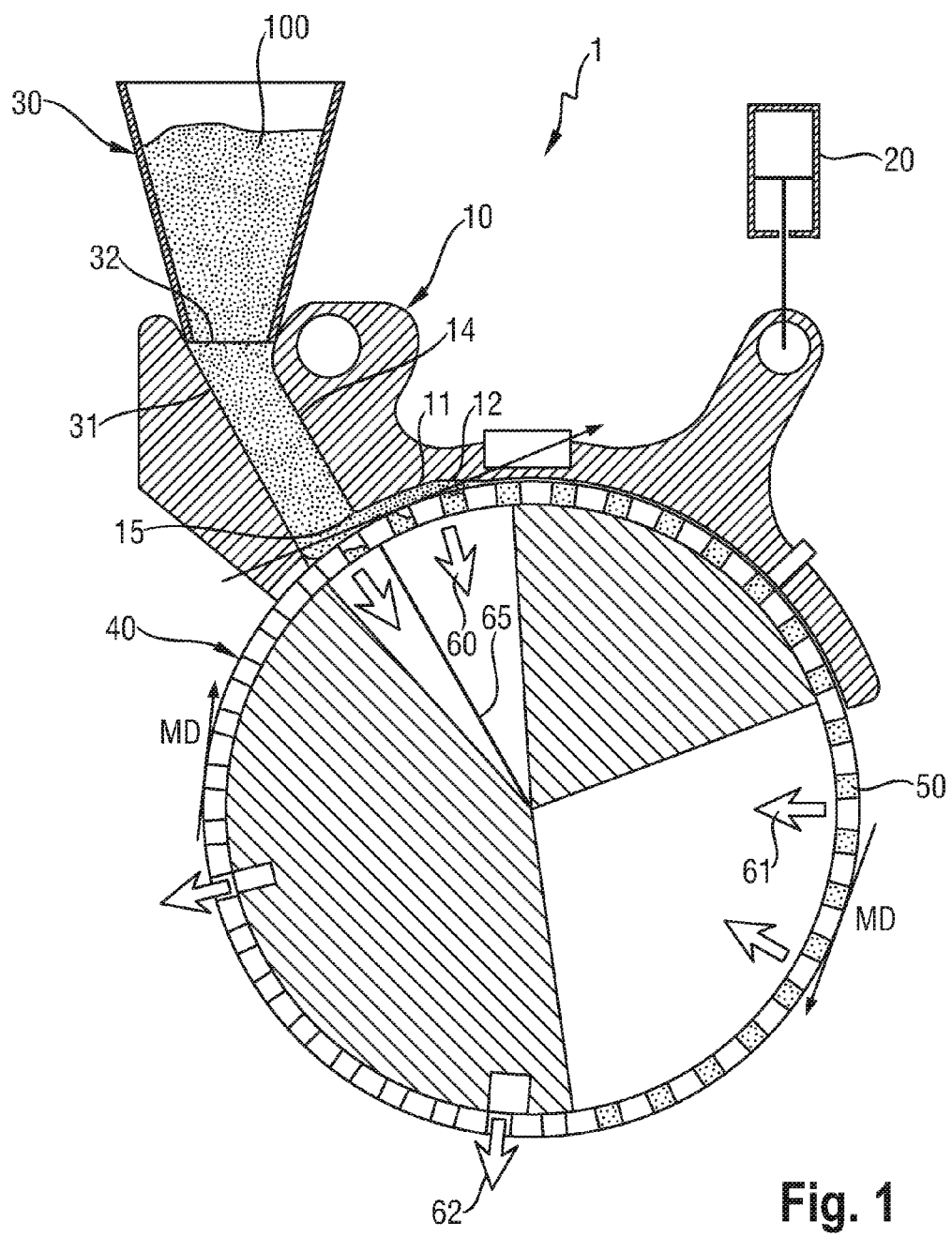
FIG. 1 shows a cross sectional (cross section taken along MD and along the direction perpendicular thereto; e.g. side view) view of a portion of an exemplary apparatus (1) of the invention.

The particulate material (100) herein may be any material in particulate form, e.g. flowable in dry state, which includes particles, flakes, fibers, spheres, agglomerated particles and other forms known in the art.

In some embodiments herein, the particulate material (100) is particulate absorbent (or: superabsorbent) material, and this material is typically polymeric, and also known as particulate absorbent gelling material, herein referred to as AGM. This refers to polymeric materials in particulate form that can absorb at least 10 times their weight of a 0.9% saline solution, i.e. having a CRC value of at least 10 g/g as measured using the Centrifuge Retention Capacity test of EDANA (European Disposables and Nonwovens Association), test method No. 441.2-02 "Centrifuge retention capacity". The particulate AGM herein may have a high sorption capacity, e.g. having a CRC of for example at least 20 g/g, or at 30 g/g. Upper limits may for example be up to 150 g/g, or up to 100 g/g.

The particulate AGM may have a good permeability for liquid, for example, having a SFC value of at least $10 \times 10^{-7}$ $cm^3$ s/g; or preferably at least $30 \times 10^{-7}$ $cm^3 \cdot s/g$, or at least $50 \times 10^{-7}$ $cm^3$ s/g $10 \times 10^{-7}$ $cm^3$ s/g, or possibly permeability SFC value of at least $100 \times 10^{-7}$ $cm^3$ s/g, or at least a SFC of $120 \times 10^{-7}$ $cm^3$ sec/g. This SFC is a measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution). Upper limits may for example be up to 350 or up to 250 ($\times 10^{-7}$ $cm^3 \cdot s/g$).

In some embodiments herein the polymers of said AGM are internally cross-linked and/or surface crosslinked polymers.

In some embodiments herein, the aprticualte material herein is absorbent material comprising or consisting of particles of polyacrylic acids/polyacrylate polymers, for example having a neutralization degree of from 60% to 90%, or about 75%, having for example sodium counter ions, as known in the art, e.g. surface crosslinked and/or internally crosslinked and/or post-crosslinked polyacrylic acid/polyacrylate polymers.

In some embodiments herein, the particulate material (100) is in the form of particles with, a mass medium particle size up to 2 mm, or between 50 microns and 2 mm or to 1 mm, or preferably from 100 or 200 or 300 or 400 or 500 μm, or to 1000 or to 800 or to 700 μm; as can for example be measured by the method set out in for example EP-A-0691133. In some embodiments of the invention, the particulate material (100) is in the form of particles whereof at least 80% by weight are particles of a size between 50 μm and 1200 μm and having a mass median particle size between any of the range combinations above. In addition, or in another embodiment of the invention, said particles are essentially spherical. In yet another or additional embodiment of the invention the particulate material (100) has a relatively narrow range of particle sizes, e.g. with the majority (e.g. at least 80% or preferably at least 90% or even at least 95% by weight) of particles having a particle size between 50 μm and 1000 μm, preferably between 100 μm and 800 μm, and more preferably between 200 μm and 600 μm.

The particulate material (100) herein may advantageously comprise less than 15% by weight of water, or less than 10%, or less than 8% or less than 5%. The water-content can be determined by the Edana test, number ERT 430.1-99 (February 1999) which involves drying the particulate material (100) at 105° Celsius for 3 hours and determining the moisture content by the weight loss of the particulate material (100) after drying.

The particulate AGM herein may be particles of AGM that are surface coated or surface treated (this not including surface-crosslinking, which may be an additional surface-treatment); such coatings and surface treatment steps are well known in the art, and include surface treatment with one or more inorganic powders, including silicates, phosphates, and coatings of polymeric material, including elastomeric polymeric materials, or film-forming polymeric materials.

Substrate

The (e.g. absorbent) structure producible with the apparatus (1) and method of the invention comprises a substrate, to receive the particulate material (100). This substrate may be any sheet or web material, in particular paper, films, wovens or nonwovens.

In some embodiments herein, the substrate is a nonwoven, e.g. a nonwoven web; nonwoven, when used herein, refers to a manufactured sheet or web of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). The fibers may be bicomponent fibers, for example having a sheet-core arrangement, e.g. with different polymers forming the sheet and the core. Nonwoven fabrics can be formed by many processes such as meltblowing, spunbonding, solvent spinning, electrospinning, and carding. The basis weight of nonwoven fabrics is usually expressed in grams per square meter (gsm).

The nonwoven herein may be made of hydrophilic fibers; "Hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally co-existing. Conversely, a fiber or surface of the fiber is considered to be hydrophobic if the contact angle is greater than 90° and the fluid does not spread spontaneously across the surface of the fiber.

The substrate herein may be air-permeable. Films useful herein may therefore comprise micro pores. Nonwovens herein may for example be air permeable. The substrate may have for example an air-permeability of from 40 or from 50, to 300 or to 200 $m^3/(m^2 \times min)$, as determined by EDANA method 140-1-99 (125 Pa, 38.3 $cm^2$). The substrate may alternatively have a lower air-permeability, e.g. being non-air-permeable, to for example be better detained on a moving surface comprising vacuum.

In preferred executions, the substrate is a nonwoven material, a nonwoven web, for example of the SMS or SMMS type, and it may have a CD-extensibility or a MD-extensibility, for example of more the 20%, or for example more than 100%, but for example not more than 200%. The ratio of MD-extensibility to the CD-extensibility is at a given load not more than one to two.

Further exemplary absorbent structures and cores are described herein below.

Apparatus

The apparatus (1) of the invention comprises at least the following components: a feeder (30) for feeding particulate material (100) to a moving endless surface with reservoirs (50); said moving endless surface with reservoirs (50), for receiving said particulate material (100) and transferring it to a substrate; a three-dimensional plate (10) adjacent said surface and adjacent said feeder (30); and a support, typically a second moving endless surface (110, 200), for carrying or transporting a substrate, for receiving said particulate material (100) from said first moving endless surface (40) with reservoirs (50).

An exemplary apparatus (1) is shown in FIG. 1, showing the feeder (30), first moving endless surface (40) with reservoirs (50), and a second moving endless surface (200), e.g. substrate (110), or a substrate that may be supported on a second moving endless surface (200), whereby said first moving endless surface (40) rotates and thereby transfers the particulate material (100) from the meeting point adjacent the feeder (30) towards a transfer point where the particulate material (100) is transferred to said substrate.

The apparatus (1) may comprise additional components or modules, upstream and/or downstream from the feeder (30) and first moving endless surface (40). Each of these components, and optional additional components, are now described in detail Feeder (30)

The feeder (30) herein is capable of holding the particulate material (100), typically in bulk quantities, and letting it flow to said first moving endless surface (40). The point or area where the particulate material (100) leaves the feeder (30) is herein referred to as meeting point or area.

The feeder (30) may have any form or shape. The feeder (30) may have a container portion, to hold the particulate material (100), e.g. having a volume of at least 1000 $cm^3$, and a guiding portion, e.g. a pipe-shapes portion, having one or more walls (31) that guides the particulate material (100) from the container portion to the moving endless surface. In some embodiments it has a funnel shape, as shown for example in FIG. 1, having a container portion and a pipe-shaped portion.

The wall(s) (31) of the guiding portion maybe a unitary with the container portion, or a separate portion, connected to the container portion.

In some embodiments, as exemplified as well in the figures, the three-dimensional plate (10) described herein after, has a second plate face (14) with fourth surface area that forms a guide wall for the particulate material (100), and it opposes a wall (31) from the feeder (30).

The feeder (30) has an opening (32), for allowing exit of said material towards the moving endless surface, said opening (32) having opening edges positioned adjacent the first moving endless surface (40), and typically in proximity thereto. In some embodiments, as also exemplified in FIGS. 1 and 2, the opening (32) of the feeder (30) may be taken to be the opening (32) of the pipe-shaped portion of the feeder (30), positioned adjacent (e.g. above) the first moving endless surface (40).

The average distance between said opening edges and said first moving endless surface (40) may be for example less than 10 cm, or less than 5 cm, and it may for example be less than 2 cm or less than 1 cm, and for example at least 0.1 mm, or at least 1 mm.

The opening (32) may have any form, including circular or oval; in some embodiments, the opening (32) is rectangular.

Figure 2:
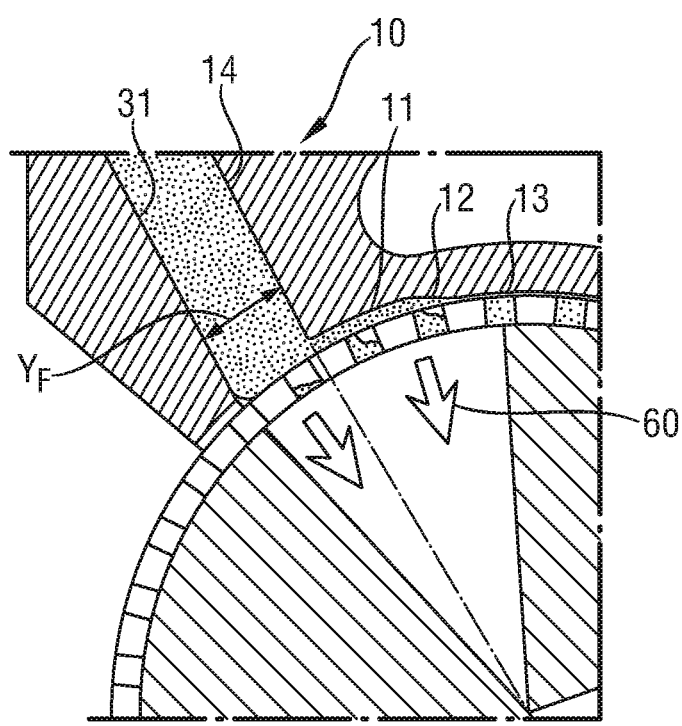
FIG. 2 shows cross sectional (as above) view of a part of the apparatus (1) as shown in FIG. 1, showing an exemplary plate (10) and its plate faces.

The guiding portion and/or the opening (32) of the feeder may have an average dimension in direction of movement (MD), indicated in FIG. 2 as Yf, of for example at the most 140 mm, or for example at the most 80 mm or at the most 60 mm; and typically for some embodiments of the invention related to specific preferred particle size particulate material (100) specified above, at least 10 mm.

In the direction perpendicular to the direction of movement, the opening (32) may have an average dimension about at least 60% of to the width of the first moving endless surface (40), or about equal to said width.

Figure 5:
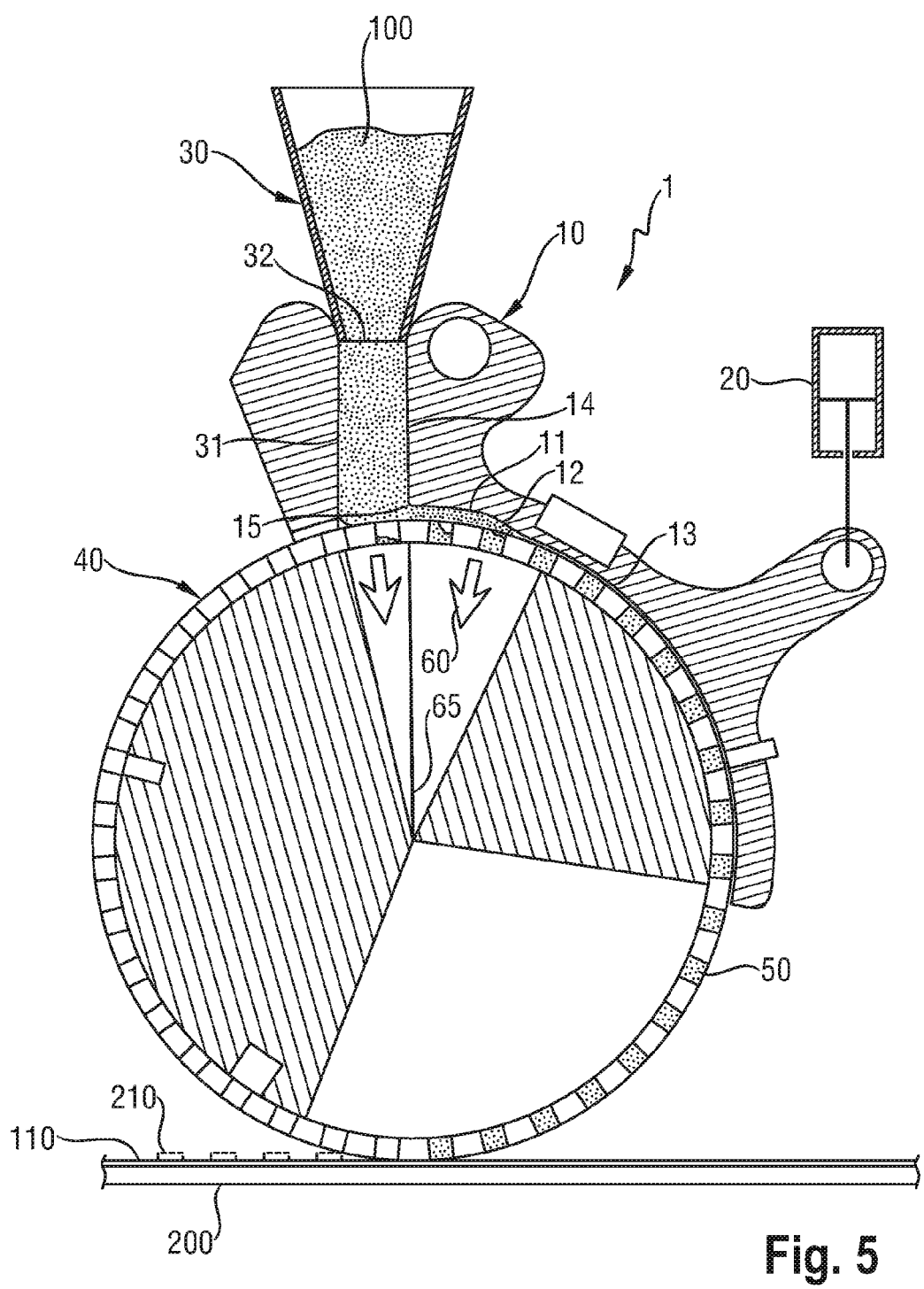
FIG. 5 shows a cross sectional view of a further apparatus (1) of the invention (cross section taken along MD and along the direction perpendicular thereto, e.g. along the line of gravity).

In some embodiments, the feeder (30) is positioned above said first moving endless surface (40), for allowing gravity to help to "feed" said particulate material (100) to said first moving endless surface (40). Hereto, an opening edge of the feeder (30) may be positioned exactly above the first moving endless surface (40) (0°), or, when the first moving endless surface (40) is curved, or even for example circular, as shown in the figures, it may be positioned above said surface, which means at any position between 90° and −90° (e.g. between 9 o'clock and 3 o'clock position), or in some embodiments between 60° and −60°, or between 30° and −30° (measured as angle between an distal edge of the opening (32) and the force line of gravity). FIG. 5 shows for example a feeder (30) positioned exactly above the first moving endless surface (40), whilst FIG. 1 shows a feeder (30) positioned at 30° position (11 o'clock position).

In some embodiments, the side wall or walls (31) are (substantially) parallel to the force line of gravity, so that said particulate material (100) can flow freely to said first moving endless surface (40). This is for example shown in FIG. 5.

Figure 3:
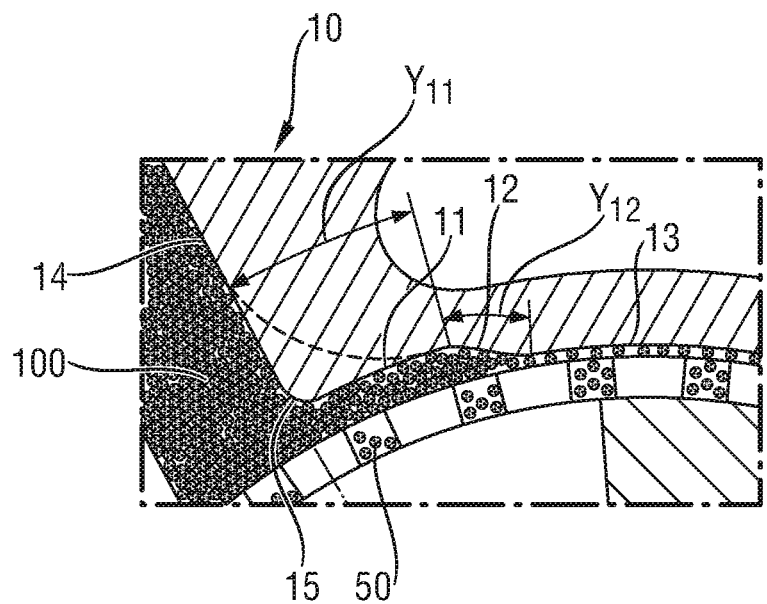
FIG. 3 shows cross sectional (as above) view of an alternative apparatus (1) of the invention with an exemplary plate (10) and its plate faces.
Figure 4:
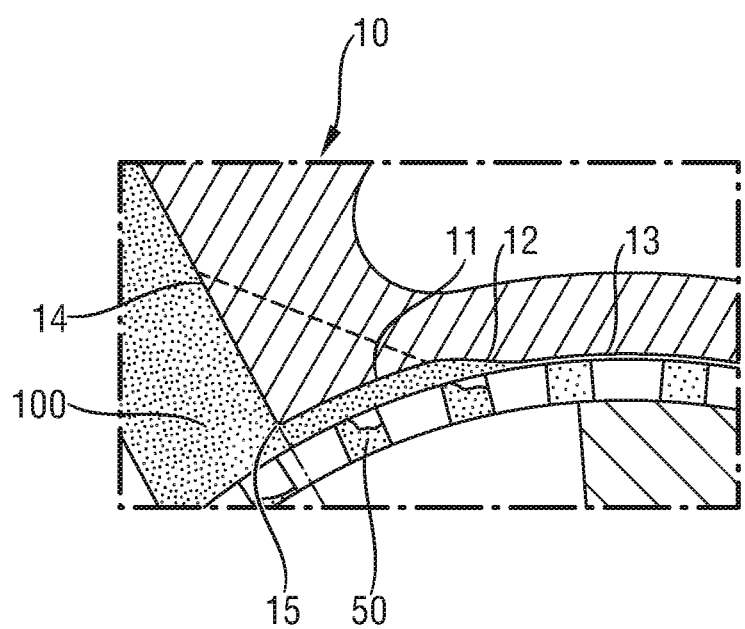
FIG. 4 shows cross sectional (as above) view of an alternative apparatus (1) of the invention with an exemplary plate (10) and its plate faces.

In some embodiments, as shown in all Figures except FIG. 3, the feeder's container portion is in contact with or close proximity with the plate (10), and said plate (10) (e.g.

the plate's second plate face, with fourth surface area (14), as described herein after), forms a guiding wall (31) for the particulate material (100), together with the wall(s) (31) of (the guiding portion of) the feeder (30). Thus, said particulate material (100) may also fall along and typically in contact with a surface (e.g. the second plate face or fourth surface area (14)) of said plate (10), described herein after. In this case, the opening (and Y f) is defined by the edge of the guiding means wall (31) and the edge of the plate's second plate face.

In another embodiment, said feeder (e.g. guiding portion) may have a wall (31) that is in contact with a surface of the plate (10), e.g. with said second plate face with said fourth surface area (14), described herein after; in some embodiments, the feeder (30) has then also a side wall (31) in contact with and parallel to the plate's fourth surface area (14); such a feeder (30) and plate (10) arrangement is for example shown in FIG. 3. Said side wall may be (substantially) perpendicular to the direction of movement (MD) of said surface (in the point of said first moving endless surface (40) that is adjacent said wall).

First Moving Endless Surface (40)

The first moving endless surface (40) herein may be any moving surface that can rotate to provide a moving endless surface, for example it may be a transporter belt or a cylinder or drum or print roll, as known in the art, which can rotate and thus provide an endless surface.

The first moving endless surface (40) has a direction of movement of said surface, herein referred to as MD. "Direction of movement (MD)" of said first moving endless surface (40), is herein to be taken to be the direction of movement in a certain point of said surface or the average direction of movement in a certain specified area of said surface, as specified herein. Thus, for a curved, e.g. circular, first moving endless surface (40), the direction of movement in a certain point of the surface, or the average direction of movement of a certain area of said surface, is herein determined by determining the tangent in said point or the average tangent of an area (then, said tangent being the average direction of movement in said area). This is for example shown in FIGS. 7 and 8. Said tangent is, as shown, perpendicular to the radius of curvature in said point or perpendicular to the average radius in said surface area, respectively.

The first moving endless surface (40) is typically a rotating device with a certain radius, such as a cylinder or drum, as for example shown in the Figures. The radius of the first moving endless surface (40) may depend on what structure is produced, and what size of structure is produced, and for example how many structures are produced per cycle of the first moving endless surface (40), e.g. drum. For example, the drum may have a radius (65) of at least 40 mm, or of at least 50 mm; it may be for example up to 300 mm, or up to 200 mm.

The first moving endless surface (40) may have any suitable width, but for example a width (perpendicular to MD) corresponding (substantially) to the width of the structure to be produced; this for example be at least 40 mm, or at least 60 mm, or for example up to 400 mm, or up to 200 mm.

It may be useful that the first moving endless surface (40) has opposing lateral zones and a central zone therein between, along the whole surface in MD, and said reservoirs (50) are only present in said central zone. Then, the width dimensions of the surface may apply to the width of the central zone instead.

It should be understood that for purpose of determination of properties of the first moving endless surface (40), such as the MD, the radius, the width of said first moving endless surface (40), the surface area where no reservoirs (50) are present (the area between reservoirs (50)) is used for such determinations. This surface area between reservoirs (50) is herein referred to as "outer surface area" of said first moving endless surface (40). Thus, in some embodiments, the first moving endless surface (40) is a drum with a surface with reservoirs (50), said reservoirs (50) protruding into said drum, and being surrounded by said outer surface area.

The reservoirs (50) may have any dimensions and shape, including cubical, rectangular, cylindrical, semi-spherical, conical, or any other shape. The first moving endless surface (40) comprises reservoirs (50) with a void volume that can be filled with particulate material (100). This may be any suitable number of reservoirs, but for example at least 20 or at least 50.

The reservoirs (50) may be present as identical reservoirs (50), or they may vary in dimension(s) or shape. They may be present in a pattern over the surface of said first moving endless surface (40), or they may be present uniformly over said surface. The exact reservoir (50) pattern, dimensions etc. will depend on the required structure to be formed, but may for example also depend on the particle size of the particulate material (100), process speed etc. In some embodiments at least 30% of the surface area of the first moving endless surface (40) or of said central zone thereof, described above, comprises said reservoirs (50), preferably at least 40% or at least 50%.

The reservoirs (50) may be present as lines of reservoirs (50) in MD and rows in CD, (the direction perpendicular to MD). Alternatively, they reservoirs (50) may for example be present in so-called alternating rows and/or lines (whereby alternating reservoirs (50) form a row and/or line).

The distance in MD between the centre point of a reservoir (50) (said centre point being in the plane of the outer surface of the first moving endless surface (40)) and the centre point of a neighboring reservoir (50) (in a line of reservoirs (50)) may for example be at least 3 mm, or at least 4 mm, or at least 6 mm, or for example up to 40 mm or up to 30 mm or up to 20 mm. This may apply to all such distances between neighboring reservoirs (50) in MD, or this may be an average over all such distances.

The distance in CD between the centre point of a reservoir (50) (said centre point being in the plane of the outer surface of the first moving endless surface (40)) and the centre point of a neighboring reservoir (50) (in a row of reservoirs (50)) may for example also be as above.

Said lines may extend substantially parallel to, and equally spaced from, one another and/or said lines may extend substantially parallel to, and equally spaced from, one another.

In some embodiments, the MD dimension of a reservoir (50) may be (on average over all reservoirs (50) and/or for each reservoir; measured over the outer surface of the first moving endless surface (40)) at least 1 mm, or at least 2 mm, or at least 4 mm, and for example at the most 20 mm or at the most 15 mm. The CD dimension may be within the same ranges as above, or it may even be the same as the MD dimensions for one or more or each reservoir.

The reservoirs (50) may have any suitable dept dimension, and it may depend for example on the height of the first moving endless surface (40) (e.g. radius), the thickness/caliper of the desired structure to be produced, the particle size of the material, etc. The maximum depth of a reservoir (50) and/or of all reservoirs (50), and/or the average maximum depth (average over all maximum depths of all reservoirs (50)) may for example be at least 1 mm, or at least 1.5 mm, or for example 2 mm or more, and for example up to 20 mm, or up to 15 mm, or in some embodiment herein, up to 10 mm, or to 5 mm or to 4 mm or to mm.

According to some embodiments herein, the reservoirs (50) may have a dimension in MD (average; and/or all reservoirs (50)) of from 2 to 8 mm or from 3 mm to 7 mm; and the reservoirs (50) may have a maximum depth and/or average maximum depth of for example from 1.5 mm to 4 mm, or to 3 mm.

The first moving endless surface (40) is adjacent the feeder (30) and adjacent the plate (10) and preferably adjacent said substrate, as described herein. It rotates such that it passes the feeder (30), to receive the particulate material (100) in its reservoirs (50), in a meeting point or area, to then carry said particulate material (100) ("downstream") to a transfer point or area, where the particulate material (100) leaves said first moving endless surface (40), in some embodiments, directly to or towards said second moving endless surface (110, 200); said second moving endless surface (200) may be a moving substrate (110) or a substrate (110) on a moving support.

One possibility to hold the particulate material (100) in the reservoirs (50) may be a vacuum (60) applied to the inner side of the first moving endless surface (40), e.g. drum, in combination with suction holes in (the bottom) of the reservoirs (50), to thus apply the vacuum suction onto the particulate material. The vacuum suction is for example exemplified with the arrows (60) and (61) in the Figures. The vacuum (60, 61) is for example released just before or at the transfer point, e.g. the point where the first moving endless surface (40) is adjacent and opposing said second moving endless surface (110, 200) (as shown with arrow 62). The vacuum (60) may be any vacuum pressure such as for example at least 10 kPa, or at least 20 kPa.

The vacuum (60) may be provided by providing a plurality of vacuum chambers in said first moving endless surface (40) (e.g. in its interior), where vacuum (60) can be applied or released (e.g. indicated by arrow (62)) (connected or disconnected), depending on the position thereof in the process, e.g. when the vacuum chamber reaches the transfer point, the vacuum may be disconnected (62) and the particles can flow from the surface to the substrate, whilst when said chamber reaches the meeting point where the particulate material (100) flows from the feeder (30) to the reservoirs (50), the vacuum (60) is applied (connected).

Additional air pressure may be applied to said particulate material (100) close to or at the transfer point, to ensure that the material flows from the reservoir (50) to the second moving endless surface (110, 200).

In some embodiments, further described below, the plate (10) face adjacent the first endless moving surface has a third surface area (13) in close proximity to and substantially parallel to said first moving endless surface (40), that aids the retention of the particulate material (100) in said reservoirs (50), since it serves as a "cover" of said reservoirs (50). Thereto, said third surface area (13) may be large, as described below, in order to retain said particulate material in said reservoirs (50) up to or close to said transfer point. This is for example exemplified in FIGS. 7 and 8.

Three-Dimensional Plate

The present invention provides improved reservoir (50) filling by use of specific pressure means. In some embodiments of the invention, a three dimensional plate (10) is therefore employed, said plate (10) being positioned downstream from the meeting point/area, and being present adjacent said feeder (30) and adjacent said first moving endless surface (40). Thus, the feeder (30) is positioned before the plate (10), in direction of the process, e.g. in the direction of movement of the first moving endless surface (40) (MD). Thus, it should be understood that at least part of the particulate material (100) contacts the first moving endless surface (40) typically prior to contacting the first surface area (11) of the plate (10).

The plate (10) has a "plate face" which is the surface of said plate (10) adjacent and (substantially) facing said first moving endless surface (40) (opposing it).

The plate (10) face comprises at least a first surface area (11) and second surface area (12) that are connected to one another under an angle, e.g. a "rounded angle", as for example shown in FIGS. 1 and 2, or a straight (true) angle, e.g. with the angle as described below.

In some embodiments, as for example shown in FIGS. 1 and 2, said plate face is a curved side of the plate (10), comprises a first surface area (11), and a second surface area (12), connected to one another with a curvature, herein referred to also as "rounded" angle, with an average "angle", as described herein below; when present, the third surface area (13) may also be connected to the second surface area with a curvature with an average are rounded angle, as described below.

Figure 7:
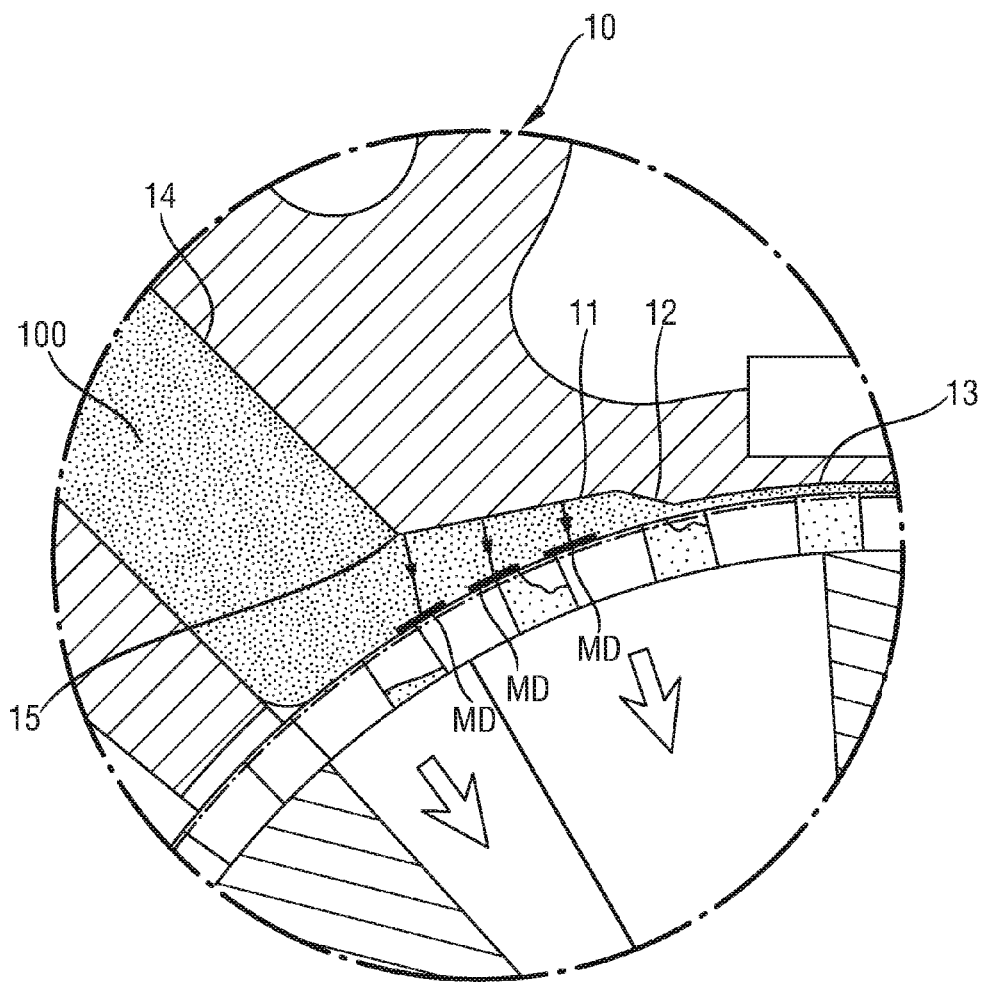
FIG. 7 shows cross sectional view (as above) of an alternative apparatus (1) of the invention with an exemplary plate (10) and its plate faces.

In addition, or alternatively, the plate face may comprise first and second surface areas, connected to one another with an angle, e.g. via an edge with an angle, as for example shown in FIG. 7; and for example a third surface area, for example connected to said second surface area (12) with an edge with an angle, as shown in FIG. 7.

However, in some embodiments it is preferred that the first and second surface areas, and/or when present said second and third surface areas, and/or, when present, said first and fourth surface areas, are (e.g. all) connected with one another under a "rounded angle", e.g. a curvature, so that the connection between the surface areas forms a curvature, as for example shown in FIG. 7.

The plate face comprises a first surface area (11), that is opposed to and adjacent said first moving endless surface (40) and that is substantially parallel to said first moving endless surface (40).

When stated herein that "the first surface area (11) is substantially parallel to the first moving endless surface (40)", this means that; 1) said first surface area (11) is parallel to the opposing surface area of said first moving endless surface (40) (which is the area where said first surface area (11) overlaps said first moving endless surface (40)), as for example shown in FIGS. 1, 2 and 3; or 2) said first surface area (11) and said opposing surface area of said first moving endless surface (40) are positioned under and average angle of at the most 30° or in some embodiments herein typically at the most 20°, as for example shown in FIG. 7. In the latter case, the first surface area (11) should be positioned such that the edge thereof closest to the feeder (30) (upstream edge) is further removed from the first moving endless surface (40), than the edge connected to the second surface (downstream edge).

Irrespective of whether the first surface area (11) is parallel or substantially parallel to the opposing first moving endless surface (40), in some embodiments, it may be preferred that the first surface area (11) is an even surface, and/or a smooth surface.

In some embodiments, the distance between the first surface area (11) and the opposing area of the first moving endless surface (40) is on average less than 15 or less than 10 times the maximum or mean particle size of the particulate material (100), but at least equal to at least twice or at least four times said mean particle size, and/or at least one or at least twice the maximum particle size. In some embodiments, the average distance may vary depending on the amount of particulate material (100) present under the first surface area (11) of said plate face, as described herein below in more detail. Then, the above average distance may be applicable under a certain pressure, or it may be the average distance at the average operating pressure, for example at 2.5 bar. In some embodiments, the average distance is equal to or more than the (e.g. average) maximum depth of the reservoirs (50), e.g. for example at least 1.2 times or 1.4 or 1.5 times.

Said first surface area (11) of the plate face is in proximity to the first moving endless surface (40), defining a volume between said first surface area (11) and said first moving endless surface (40), wherein during the process particulate material (100) is present. Said first surface area (11) then applies a pressure onto said particulate material (100), or part thereof, to guide (or optionally force, or push) it into said reservoirs (50). Said pressure and direction of pressure perpendicular to first surface area (11) is for example shown by the arrows in FIGS. 7 and 8. In some embodiments herein said pressure applied by said first surface area (11) is substantially perpendicular (as for example shown in FIG. 7) or perpendicular (as for example shown in FIG. 8) to the direction of movement (MD) of said first moving endless surface (40).

When stated herein that the pressure applied by said first surface area (11) of said plate (face) on said particulate material (100) is "substantially perpendicular to the direction of movement" of said first moving endless surface (40), this means herein that the average direction of pressure of said first surface area (11) (taken to be the direction perpendicular to the average first surface area (11) direction) is perpendicular to the average direction of movement of the opposing surface area of said first moving endless surface (40), or that that said average direction of pressure of the first surface area (11) is under an angle of at least 60°, or typically at least 70°, with said average direction of movement of said opposing surface area.

In some embodiments herein, said first surface area (11) may be parallel to said first moving endless surface (40) that it opposes (overlaps); if said first moving endless surface (40) is curved, having a certain radius, e.g. being a drum with a certain radius, the radius of curvature of said first surface are may be about the same, e.g. within 20% or within 10% of one another. In some embodiments herein, the first surface area (11) is curved, having a radius of curvature identical to the radius of curvature of said first moving endless surface (40) (e.g. drum radius).

The plate face may have a width about equal to the width of the first moving endless surface (40), or the central zone thereof.

The first surface area (11) of the plate face may have a length or average length, in MD, of for example at least 2 mm, or at least 4 mm, or at least 6 mm or at least 10 mm.

Alternatively, or in addition the first surface area (11) may have length in MD of at least equal to the dimension of the average distance between the centre points of neighboring reservoirs (50) in MD, as defined herein, preferably at least 1.5 times said dimension of said distance, or at least 2 times said dimension of said distance or at least 2.5 times said dimension of said distance.

Alternatively, or in addition the first surface area (11) may have length in MD that is at least equal to the average reservoir dimension in MD, as defined herein, preferably at least 1.5 times said dimension, or at least 2 times said dimension or at least 2.5 times said dimension or at least 3 times said dimension.

When said first surface area (11) is connected to said second surface area (12) with a curvature, as described above, then said dimension of said first surface area (11) is delimited by the centre line of said curvature, as for example shown in FIG. 3 as $Y_{11}$. The same applies for the dimensions in MD of the second and third and fourth surface area (14), herein after.

The plate face also comprises a second surface area (12) neighboring said first surface area (11), positioned downstream from the first surface area (11) (in MD), said second surface area (12) being non-parallel to said first moving endless surface (40) and leading from said first surface area (11) towards, but in one preferred example not completely to, said first moving endless surface (40), said first surface area (11) and said second surface area (12) are connected under an angle to one another, said second surface area (12) having an average angle with said first moving endless surface (40) of between 10° and 80° (said angle being between said second surface area (12) and said first moving endless surface (40) defining the area where the particulate material (100) is present during the process); in some embodiments the angle is less than 60° or less than 50°. In some embodiments, the angle is at least 20° or at least 30°, or in some embodiments, at least 40°; such larger angle can be seen in FIG. 8.

In one preferred embodiment, the first surface area (11) is parallel to the opposing first moving endless surface (40) and said second surface area (12) is under an angel as defined above.

The second surface area (12) can apply a pressure that is non-perpendicular to the direction of movement of the first moving endless surface (40). When stated herein that the pressure applied by said second surface area (12) of said plate (face) on said particulate material (100) is "a pressure non-perpendicular to the direction of movement of the first moving endless surface (40)", is meant that the average direction of pressure by said second surface area (12) (taken to be the direction perpendicular to the average second surface area (12) direction) is under an angle of less than 60° with the average MD in the area of said first moving endless surface (40) opposing (overlapped) said second surface area. Typically, the average pressure is however not parallel to MD, e.g. said angle is at least 10°.

The second surface area (12) may be a straight or curved surface area. It may be preferred to have a smooth surface.

The second surface area (12) of the plate face may have a length or average length, in MD, of for example at least 2 mm, or at least 4 mm, or at least 6 mm. Alternatively, or in addition the second surface area (12) may have length in MD of at least equal to the dimension of the average distance between the centre points of two neighboring reservoirs (50) in MD, as defined above, preferably at least 1.5 times said dimension of said distance. Alternatively, or in addition the second surface area (12) may have length in MD that is at least equal to the average dimension of a reservoir (50) in MD, as defined herein, preferably at least 1.5 times said dimension.

The first surface area (11) and second surface area (12) are connected under an angle i.e. connected via an edge with a certain angle (as shown in FIG. 7 for example) or connected by a curved area/curvature with an average "angle", as for example shown in all other Figures. For example, the angle or average "angle" between the first and second surface area

(12) may be from 100° to 170°; or at least 120° or at least 130°, and preferably less than 160° or less than 150°.

The plate face may have a third surface area, substantially parallel to the first moving endless surface (40), as defined above for the first surface area (11); or, in some embodiments, parallel to said first moving endless surface (40), or under an (average angle of less than 10° or less than 5°.

The third surface area (13) is in close proximity, or optionally partially in contact with, said first moving endless surface (40). In any event the third surface area (13) of the plate face is closer to said first moving endless surface (40) than said first surface area (11) of the plate face.

Figure 8:
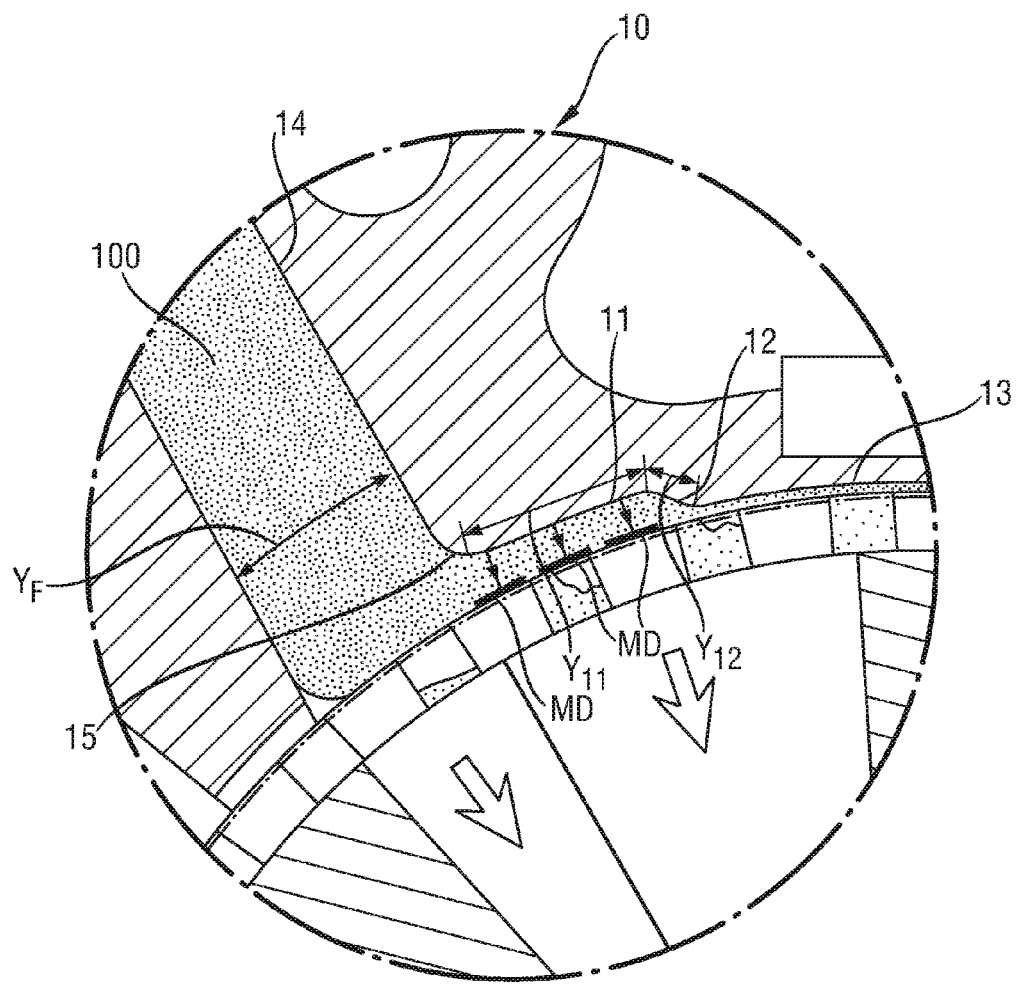
FIG. 8 shows cross sectional view (as above) of an alternative apparatus (1) of the invention with an exemplary plate (10) and its plate faces.

The average distance between the third surface are and the first moving endless surface (40) may be less than a 2 mm, or less than 1 mm; in some embodiments, it may be less than 0.5 mm. Alternatively, or in addition, the average distance may for example be about equal or less than the maximum particle size of the particle material. For example FIG. 8 shows how the third surface area (13) is spaced from the first moving endless surface (40) such that some particulate material (100) may still be present in the space between the third surface are and said first moving endless surface (40), said average distance being for example (slightly) more than or about the mass mean particle size of the particulate material (100).

The third surface area (13) may have a length in (MD) of for example at least 2 mm, or at least 4 mm, or at least 6 mm, or at least 10 mm, or at least 20 mm or at least 30 mm.

As mentioned above, the third surface area (13) may serve as a "closure" for said reservoirs (50), to ensure said particulate material (100) remains in said reservoirs (50). The third surface area (13) may then be for example at least 4 times or at least 8 times or at least 12 times the (average) reservoir (50) dimension in MD, and/or of the dimension of the distance between the centre points of two neighboring reservoirs (50) in MD, as above.

The plate is positioned adjacent and downstream of the feeder (30), so that the plate can contact the particulate material (100) directly after release thereof by the feeder (30) (to or towards the first moving endless surface (40)). The position of the plate in the apparatus (1) is thus to a large extend determined by the position of the feeder (30), e.g. by the position of the feeder (30) guiding portion and/or wall(s) (31). In some embodiments, the position of the plate (10) in the apparatus (1) may be such that the outer edge/curvature (15) of the plate face's first surface area (11) is positioned substantially above the first moving endless surface (40), e.g. directly above the feeder (30), or under and angle, as defined herein above, of for example 60° to −90° (3 o'clock) or to −60°, or 30° to −60° or −30°.

The plate may have a second plate face, not opposing the first moving endless surface, that comprises a fourth surface area (14), being adjacent or neighboring or in close proximity or even connected to said feeder (30) (said fourth surface area (14) is thus not part of the plate face comprising said first, second and optional third surface area, but (a part of) another side of the plate (10), e.g. herein referred to as second plate face).

The fourth surface area/second plate face are, typically directly, neighboring and hence connected to said first surface area (11), for example under and angle, or curvature (15) with an average "angle" of for example at least 70° or at least 80°, and up to 110° or 100°, and for example about 90°.

Said second plate face (14) or said fourth surface area (14) may optionally be contacting and guiding said particulate material (100) towards said first moving endless surface (40), as described above.

When the plate (10) is movable during the process, e.g. in responds to changing pressure, the fourth surface area (14) may not be attached to the feeder (30), but only in close proximity thereto.

Figure 6:
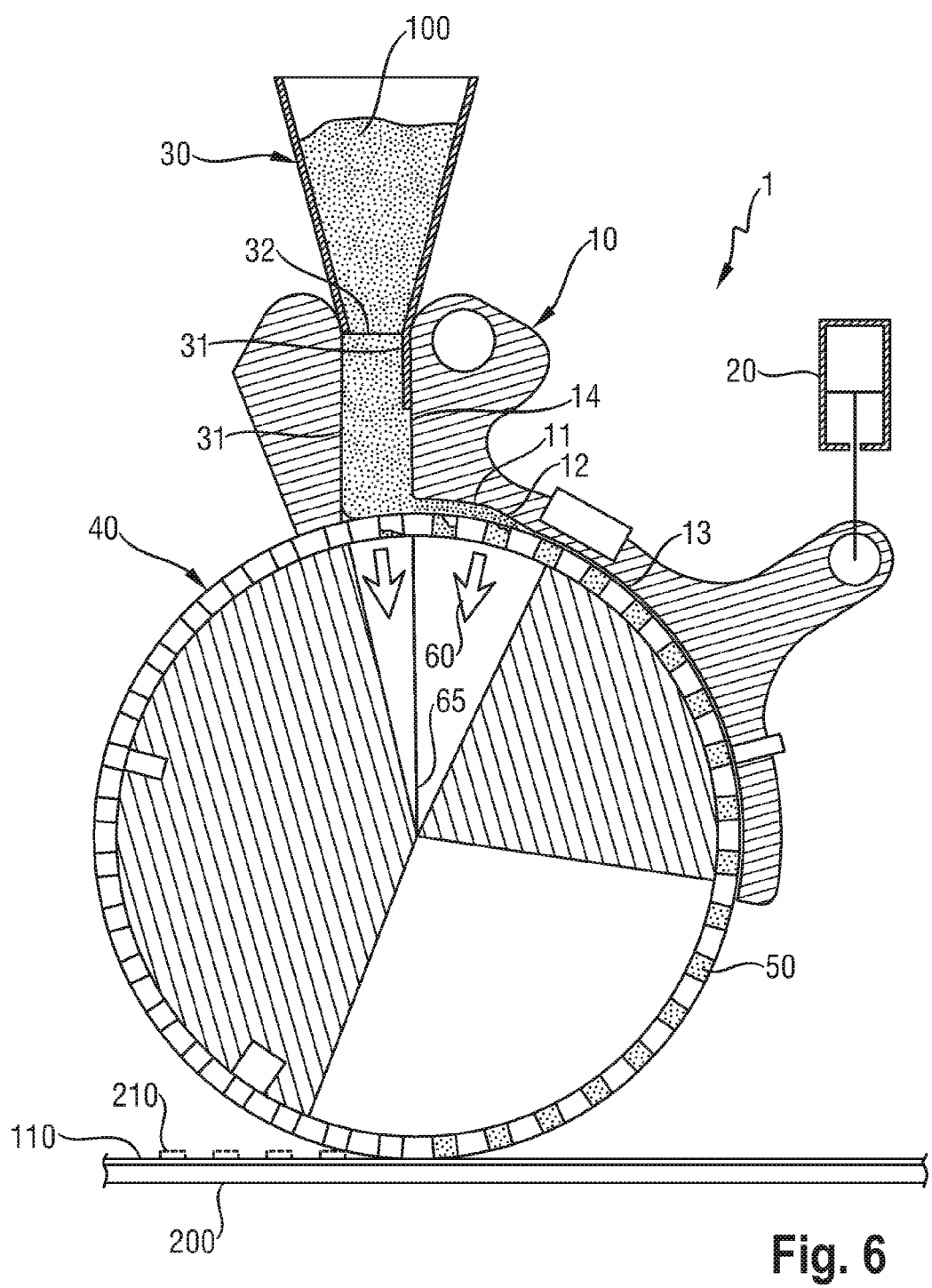
FIG. 6 shows a cross sectional view of a further apparatus (1) of the invention (cross section taken along MD and along the direction perpendicular thereto, e.g. side view).

The fourth surface area (14)/second plate face may be positioned to be an extension to a feeder (30)'s container portion, guiding the particulate material (100) from the container portion towards the first moving endless surface (40), as shown in for example FIGS. 1 and 5. Alternatively, the fourth surface area (14)/second plate face may be positioned to be an extension to a feeder (30)'s guiding portion, e.g. wall (31) and then the particulate material (100) is guided from the container portion towards the first moving endless surface (40) by the feeder wall (31) and then by the fourth surface area (14) of the plate (10), as for example shown in FIG. 6.

The fourth surface area (14)/second plate face may be substantially perpendicular to the direction of movement of the first moving endless surface (40) (MD) under that fourth surface area (14)/second plate face.

The fourth surface area (14) or second plate face may for example have an average height dimension (e.g. substantially perpendicular to the direction of movement of the first moving endless surface (40)) of at least 2 mm, or at least 4 mm, or at least 6 mm, or at least 10 mm or at least 20 mm.

The (external) pressure applied by the plate (10) onto the particulate material (100), e.g. via the first plate face, may be a pressure caused by gravity; the plate (10) may thus for example have a weight of at least 500 grams, or at least 750 grams, preferably at least 1000 grams, and in some embodiments, up to 5000 grams. In such cases, the plate (10) is position above the first moving endless surface (40), as described above. In addition, or alternatively, a pressure application means may be connected to the plate (10) to apply the pressure as described herein.

In some embodiments, the plate (10) applies a certain pressure on to said particles that is controllable, e.g. it can be set to be a constant pressure, or variable over time. This is herein referred to as controlled external pressure. In some embodiments, this pressure is kept substantially constant or in a set range. This pressure range or constant pressure may be for example in the range of, for example, from 1 to 4 bar, or from 1.5 to 3.5 bar or from 1.5 to 3 bar or to 2.5 bar.

In some embodiments, the plate (10) is connected to a pressure control means, said pressure control means (20) being capable of:
  sensing the pressure onto said plate (10) face by said particulate material (100) and
  responding thereto, e.g. by: adjusting the pressure or force of said plate (10) (plate face) onto said particulate material (100).

The pressure control means (20) may include a means to adjust the average distance between the first surface area (11) of the plate face and the first moving endless surface (40), and/or means to change the external pressure.

The pressure control means (20) may be any means know in the art to maintain a certain pressure or adjust a certain pressure, including a hinge, a spring, or in particular an actuator (20).

The actuator (20) may be such that i) it senses the pressure on said plate (10) (face) by said particular material, and in response thereto ii) effects and controls movement of the plate (10) towards or away from said first moving endless surface (40).

Any actuator (20) as known in the art may be used; actuator (20) are typically mechanical, pneumatic, hydraulic or electrical device that performs a mechanical motion in response to an input signal; in the present case, it may be preferred that the pressure onto the plate by the particulate material (100) is the signal to the actuator (20), and that said pressure signal is for example translated into (mechanical) movement of said plate (10).

In some embodiments, the pressure control means (20) is such that when the particulate material (100) exerts a certain too high pressure onto said plate (10), the plate (10) moves away from the first moving endless surface (40), e.g. the distance between said first and second, and optionally third surface area and said first moving endless surface (40) increases. Thereby, the external pressure of the plate (10) may stay substantially constant, e.g. as above.

This helps to avoids that too much particulate material (100) builds up under the plate (10), and/or that the particulate material (100) gets too compacted, to be guided into the cavities, or to be removed from the apparatus (1) as excess material.

Pressure Means:

In some embodiments, the apparatus (1) comprises a first pressure means, e.g. device, being positioned adjacent said first moving endless surface (40), and adjacent or incorporated in said feeder (30), for applying pressure on at least part of, or part of, said particulate material (100), said pressure being in a direction substantially perpendicular to the direction of movement of said moving endless surface (MD), as defined herein below; and in some embodiments, substantially parallel with the direction of gravity.

The apparatus (1) then also typically comprises a second pressure means adjacent said first moving endless surface (40) and adjacent said first pressure means, and positioned downstream there from, for applying pressure on at least part of, or part of, said particulate material (100), said pressure (in an area) being in a direction non-perpendicular to the direction of movement of said moving endless surface (MD), as described below.

Said second pressure means may have a pressure-applying surface substantially non-parallel to the direction of movement of said first moving endless surface (40) (MD), and having for example an average angle with said first moving endless surface (40) of between 10° and 80°.

Said first pressure means may have a pressure-applying surface substantially parallel to the direction of movement of said first moving endless surface (40) (MD), for contacting and applying pressure onto at least part of said particulate material (100) when present between said pressure surface and said first moving endless surface (40).

The properties and specifics of the apparatus (1) and the pressure control means (20) are equally applicable to the present invention regarding the above first and second pressure means. Furthermore, the pressure means may have any of the other properties or specifics specified herein for the plate.

Furthermore, in some embodiments herein, the properties and specifics of the first surface area (11) of the plate (10) equally apply to the first pressure means above, and the properties and specifics of the second surface area (12) of the plate (10) equally apply to said second pressure means.

Second moving endless surface; and optional further apparatus components (units); resulting structures The particulate material (100) is transferred by the first moving endless surface (40) to a second moving endless surface (110, 200). This may be for example a belt or drum, or this may for example be a moving substrate (110), such as a film (e.g. film web) or such as, in some embodiments herein, a nonwoven (e.g. nonwoven web). It may for example be a substrate (110) carried on a moving endless surface such as a belt or a drum. In some embodiments, the second moving endless surface (200) is a web of substrate (110) with another component, such as an adhesive and/or particulate material (100).

The second moving endless surface (110, 200) may have the same surface speed as the first moving endless surface (40), or it may have a different speed. In some embodiments, it has a speed of at least 1000 part per minute and/or a speed of at least 4.5 m/s, or at least 6 m/s, or at least 8 m/s.

The particulate material (100) transfers from the first moving endless surface (40) (i.e. the cavities thereof) to said second moving endless surface (110, 200) in the transfer point or area. The transfer point is the point (e.g. line parallel to the width of the first moving endless surface (40)) where the particulate material (100) starts being released from the cavity and starts being transferred to the second moving endless surface (110, 200). The whole area over which the transfer takes place is herein referred to as transfer area.

In some embodiments herein, the second moving endless surface (200) is a substrate (110) carried on moving endless support, such as a roll, drum or belt. This support may comprise vacuum means and openings, through which the vacuum can be applied to said substrate (110), to retain the substrate on said support.

In some embodiments, the first moving endless surface (40) rotates and the second moving endless surface (110, 200) is for example placed positioned substantially under the first moving endless surface (40) so that the particulate material (100) can transfer in the transfer point or area to said second moving endless surface (110, 200) by gravity. The transfer point may thus be at a parallel to the line of gravity, or under an angel therewith from 60° to −60°, or from 30° to −30°.

The substrate (110) may comprise an adhesive, in order to, at least partially, adhere the particulate material (100) to the substrate (110). In order to better allow vacuum to be applied on the substrate (110) with adhesive, the adhesive may be applied in a pattern, whereby parts of the substrate (110) do not comprise adhesive and parts of the substrate (110) do comprises adhesive. The pattern may correspond to the pattern of the reservoirs (50) of the first moving endless surface (40).

After transfer of the particulate material (100) to the second moving endless surface (110, 200), said surface may move the particulate material (100) to further additional units (which may be part of the apparatus (1) of the present invention), to apply further materials to the particulate material (100) and/or the substrate (110). This may include one or more further adhesive(s), for example applied by a further (downstream) adhesive unit, and/or a further substrate (110), applied for example by a further (downstream) rotating support carrying a further substrate (110), a cutting unit etc.

In some embodiments, the second moving endless surface (200) is a substrate (110) (e.g. on a support) and after transfer of the particulate material (100) to said substrate (110), the substrate (210) moves to a unit that applies an adhesive material, and/or a thermoplastic material and/or an adhesive thermoplastic material, for example in fibrous form, to cover the particulate material (100), or part thereof.

In another or additional embodiment, the substrate with particulate material (210) moves to a unit that applies a further substrate (110) onto the particulate material (100), or optionally onto said adhesive and/or thermoplastic and/or thermoplastic adhesive material.

Said further substrate (110) may comprise adhesive on the side that contacts the particulate material (100) (or optionally said thermoplastic and/or adhesive and/or thermoplastic adhesive material), to better adhere said substrate (110) to said particulate material (100). In some embodiments, the substrate with particulate material (210) (e.g. as a layer) is moved to a further unit, where a second substrate with particulate material (100) (e.g. as a layer), e.g. made by an apparatus (1) of the invention in the manner described herein, is superposed thereon, for example such that substrate (110) and further substrate sandwich said particulate material (100), e.g. said two particulate material "layers". In some embodiments, the substrate with particulate material (210), made with an apparatus (1) of the invention and the method of the invention, is moved to a further apparatus (1) of the invention, that transfers particulate material (100) onto said substrate with particulate material (210), (optionally onto said thermoplastic and/or adhesive and/or thermoplastic adhesive material).

The apparatus (1) of the invention may thus comprise one or more units, upstream and/or downstream of said first moving endless surface (40), such as adhesive application unit(s), and/or substrate application unit(s). Such adhesive application units may be selected from any type known in the art, in particle slot coating units and spray units.

The resulting substrate with particulate material (210) may thus be a web of structures herein (optionally combined with any of the further materials described above) and it may then move to a cutting unit, that cuts the substrate with particulate material (210), e.g. web of structures, into individual structures, e.g. absorbent cores for absorbent articles, or absorbent articles or partial absorbent articles. Such absorbent cores or partial absorbent articles may then be combined with further absorbent article components, described herein below, to form a final absorbent article.

The support of said substrate (110) may comprise a grid, having for example plurality of bars extending along the direction of movement of said second moving endless surface (110, 200), and extending (substantially) parallel to and (equally) spaced from one another; and/or a plurality of cross bars extending along the direction perpendicular to the direction of movement of said second moving endless surface (110, 200), and extending (substantially) parallel to and (equally) spaced from one another; said cross bars or bars forming thus "channels" between them; or if the cross bars and bars are both present, forming "indentations" between them. The reservoirs (50) of the first moving endless surface (40) may then correspond (in the apparatus/ during the transfer process) with the islands or part of the channels and the particulate material (100) may transfer from the reservoirs (50) into said channels or into said indentations. The support grid may be a vented support grid with vacuum means, applying a vacuum between the bars and/or crossbars, and thus in the areas of the substrate (110) supported by the grid, forming the islands or channels.

In some embodiments herein, a coversheet material, in the form of a web material, is placed over the particulate material (100) on said second moving endless surface (110, 200), after transfer, to cover said particulate material (100), and typically to enclose it between said coversheet and said substrate (110).

In some embodiments, the particulate material (100) is placed in a longitudinally (MD) extending portion of the substrate (110), leaving a longitudinal (MD) extending portion free of particulate material (100). Then, the portion free of particulate material (100) may be folded onto said particulate material (100), after transfer thereof, to provide a cover thereof. In this embodiment, the substrate (110) is thus also a cover sheet. A further coversheet may be used in addition, as specified above.

The substrate (110) may be joined to itself or to a cover sheet or other component, as described above, by any means, for example by ultrasonic bonding, thermo-bonding or adhesive-bonding, e.g. for example sprayed adhesive bonding. The bonding region between the coversheet and the substrate (110), or may for example be at least 1%, or at least 2%, or for example at least 5%, but for example not more than 50% or no more than 30% of the surface area of the substrate (110). Preferably, the bonding region comprises essentially no particulate material (100).

As mentioned above, a adhesive, and/or thermoplastic or thermoplastic adhesive material may serve to at least partially cover and at least partially immobilize the particulate material (100), for example an adhesive and/or thermoplastic or thermoplastic adhesive material in fibrous form, e.g fibrous layer which is at least partially in contact with the particulate material (100) and optionally partially in contact with the substrate (110). The thermoplastic material may be a hot melt adhesive material. In accordance with certain embodiments, the thermoplastic (adhesive) material may comprise a single thermoplastic polymer or a blend of thermoplastic polymers, having for example a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. The thermoplastic polymer may have a molecular weight (Mw) of more than 10,000 and a glass transition temperature (Tg) usually below room temperature or −6° C.>Tg<16° C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins. In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic (adhesive) material may be in the form of fibers of an average thickness of about 1 to about 50 micrometers or about 1 to about 35 micrometers and an average length of about 5 mm to about 50 mm or about 5 mm to about 30 mm.

The cover layer may comprise the same material as the substrate (110), or may comprise a different material. In certain embodiments, suitable materials for the cover layer are the non-woven materials, useful for the substrate (110).

Method

The present invention also relates to a method as described above and as claimed herein. Any of the above described features of the apparatus (1) and functions and method steps thereof apply the method of the invention. In particular, in said method, the pressure application step c) includes for example: firstly applying a pressure, with said first surface area (11) of said plate (10), said pressure being substantially perpendicular to the direction of movement of the first moving endless surface (MD), thereby guiding (or optionally pushing) at least a first portion of said particulate material (100) into said reservoirs (50); and secondly, applying a pressure with said plate face's second surface area (12) said pressure being non-perpendicular to the direction of movement of the first moving endless surface (MD), thereby guiding, or optionally pushing, at least a second portion of said particulate material (100) into said reservoirs (50).

In said method, a third surface area (13) as described above, may guide, or optionally push, a third portion of said particulate material (100) into said reservoirs (50) and/or it may aid retention of said particulate material (100) in said reservoirs (50).

In the method, the pressure may be controlled by use of a pressure control means, including an actuator (20), as described above.

The method and apparatus (1) herein may produce for example at least 1000 part per minute (ppm, or at least 1100 or at least 1200; said "parts" being the individual structures described herein, e.g. for example absorbent structures.

In the method herein, said first moving endless surface (40) may have for example a surface speed of at least 2.0 m/s, or at least 3 m/s or at least 4.5 m/s, or at least 6.0 m/s, or at least 7.0 m/s, or at least 7 m/s. Alternatively, or in addition, the first surface area (11) may have a speed defined by parts per minute, of at least 500 parts per minute, or at least 1000 parts per minute. In one such embodiment, the first moving endless surface (40) is a drum, comprising cavities corresponding to one or two, preferably one (e.g. absorbent) structure herein.

The method herein may be particularly useful to make absorbent structures (including: a web thereof that may then be divided, e.g. cut, into individual absorbent structures), whereby said particulate material (100) is AGM, with a mass median particle size of from 150 to 1000 microns, or from 200 or 300 to 700 microns.

The method may employ the step to add a thermoplastic material, and/or adhesive material and/or thermoplastic adhesive material to said substrate (110) prior to transfer of said particulate material (100) and/or to the said particulate material (100) and/or substrate (110) after said transfer, and/or the step to add further substrate (s) or covering sheet(s) and/or to fold the substrate (110) and close the substrate (110) over said particulate material (100) and/or the step to add a further substrate with particulate material (100) (210), as described above.

Absorbent Cores and Absorbent Articles

The apparatus (1) and method of the invention are for example useful to produce absorbent structures, such as acquisition layers and/or absorbent cores for absorbent articles, or partial absorbent articles, for example the backsheet and core and optionally the topsheet, of such article; and/or to produce absorbent articles.

"Absorbent article" refers to devices that absorb and contain body exudates, and, more specifically, refers to devices that are placed against or in proximity to the body of the wearer to absorb and contain the various exudates discharged from the body. Absorbent articles may include diapers, including fastenable diapers and (refastenable) training pants; adult incontinence undergarments (pads, diapers) feminine hygiene products (sanitary napkins, pantyliners), breast pads, care mats, bibs, wound dressing products, and the like. "Diaper" refers to an absorbent article generally worn by infants and incontinent persons about the lower torso so as to encircle the waist and legs of the wearer and that is specifically adapted to receive and contain urinary and fecal matter. As used herein, the term "body fluids" or "body exudates" includes, but is not limited to, urine, blood, vaginal discharges, breast milk, sweat and fecal matter.

As well known in the art, the absorbent core is the portion of the article that retains absorbed bodily fluids. The absorbent core herein thus comprises the particulate material (100) that is an absorbent particulate material (100) (as defined herein) disposed on a substrate (110), formed by the apparatus (1) and method herein. The absorbent core does not include an acquisition system, a top sheet, or a back sheet of the absorbent article, which are additional components of such absorbent articles. The absorbent core is typically sandwiched between at least a backsheet and a topsheet. The absorbent cores herein may thus comprise typically a further layer, e.g. a further particulate material (100) and substrate layer (110 or 210), coversheet, or a further layer being a portion of the substrate (110) folded over said particulate material (100), as described above. The absorbent core herein may comprise adhesive and/or thermoplastic material, as described above.

In preferred embodiments herein, the absorbent core, and optionally the absorbent article, is "substantially cellulose free" is used herein to describe an absorbent core or article, that contains less than 10% by weight cellulosic fibers, or less than 5% cellulosic fibers, or less than 1% cellulosic fibers, or no cellulosic fibers.

In certain embodiments, the absorbent structure or core herein may comprise said particular absorbent (polymeric) material, e.g. AGM, in an amount greater than about 80% by weight of the structure or absorbent core, or greater than about 85% by weight, or greater than about 90% by weight of the absorbent core, or greater than about 95% by weight of the core.

According to certain embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a certain embodiment, the first and the second square are centered about the longitudinal axis.

It has been found that, for most absorbent articles such as diapers, the liquid discharge occurs predominately in the front half of the diaper. The front half of the absorbent structure herein may thus comprise most of the absorbent capacity of the core. Thus, according to certain embodiments, the front half of said absorbent structure herein may comprise more than about 60% of the particulate material (100), e.g. AGM, or for example more than about 65%, 70%, 75%, 80%, 85%, or 90% of the total amount of particulate material (100), e.g. AGM.

The absorbent article herein may comprise in addition to an absorbent core, a topsheet and backsheet, and for example one or more side flaps or cuffs. The topsheet or cuffs or side flaps may comprise a skin care composition or lotion or powder, known in the art, panels, including those described in U.S. Pat. No. 5,607,760; U.S. Pat. No. 5,609,587; U.S. Pat. No. 5,635,191; U.S. Pat. No. 5,643,588.

Preferred absorbent articles herein comprise a topsheet, facing the wearer in use, for example a nonwoven sheet, and/or an apertured sheet, including apertured formed films, as known in the art, and a backsheet, an absorbent core, having optionally a core coversheet facing the wearer in use.

The backsheet may be liquid impervious, as known in the art. In preferred embodiments, the liquid impervious backsheet comprises a thin plastic film such as a thermoplastic film having a thickness of about 0.01 mm to about 0.05 mm. Suitable backsheet materials comprise typically breathable material, which permit vapors to escape from the diaper while still preventing exudates from passing through the backsheet. Suitable backsheet films include those manufactured by Tredegar Industries Inc. of Terre Haute, Ind. and sold under the trade names X15306, X10962 and X10964.

The backsheet, or any portion thereof, may be elastically extendable in one or more directions. The backsheet may be attached or joined to a topsheet, the absorbent core, or any other element of the diaper by any attachment means known in the art.

Diapers herein may comprise leg cuffs and/or barrier cuffs; the article then typically has a pair of opposing side flaps and/or leg and/or barrier cuffs, each of a pair being positioned adjacent one longitudinal side of the absorbent core, and extending longitudinally along said core, and typically being mirror images of one another in the Y-axis (in MD) of the article; if leg cuffs and barrier cuffs are present, then each leg cuffs is typically positioned outwardly from a barrier cuff. The cuffs may be extending longitudinally along at least 70% of the length of the article. The cuff(s) may have a free longitudinal edge that can be positioned out of the X-Y plane (longitudinal/transverse directions) of the article, i.e. in z-direction. The side flaps or cuffs of a pair may be mirror images of one another in the Y-axis (longitudinal axis; MD axis) of the article. The cuffs may comprise elastic material.

The diapers herein may comprise a waistband, or for example a front waistband and back waist band, which may comprise elastic material.

The diaper may comprise side panels, or so-called ear panels. The diaper may comprise fastening means, to fasten the front and back, e.g. the front and back waistband. Preferred fastening systems comprise fastening tabs and landing zones, wherein the fastening tabs are attached or joined to the back region of the diaper and the landing zones are part of the front region of the diaper.

The absorbent article may also include a sub-layer disposed between the topsheet and the absorbent core, capable of accepting, and distributing and/or immobilizing bodily exudates. Suitable sublayers include acquisition layers, surge layers and or fecal material storage layers, as known in the art.

Other suitable components of absorbent articles include acquisition layers. Suitable materials for use as the sub-layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented, preferably looped, strands of fibers, or preferably apertured formed films, as described above with respect to the genital coversheet. (As used herein, the term "microporous" refers to materials that are capable of transporting fluids by capillary action, but having a mean pore size of more than 50 microns. The term "macroporous" refers to materials having pores too large to effect capillary transport of fluid, generally having pores greater than about 0.5 mm (mean) in diameter and more specifically, having pores greater than about 1.0 mm (mean) in diameter, but typically less than 10 mm or even less than 6 mm (mean).

The (absorbent) structure or core formed herein comprises in some embodiments a substrate with said particulate material (210), whereby said substrate (110) is C-folded to enclose said particulate material (100). In other words, the particulate material (100) may be deposited unto the substrate (110) and the substrate (110) may then be folded to cover the particulate material (100). Alternatively, or in addition, a separate sheet material, or cover sheet, may be placed over the particulate material (100) after it is deposited onto said substrate (110), to cover the particulate material (100). Such a coversheet may be any of the material described herein above as substrate (110) material, e.g. a nonwoven sheet or web.

Alternatively, or in addition, two or more of the substrates with particulate material (210) deposited thereon may be produced and placed onto one another, to cover one another. Hereby, an additional coversheet may be placed first onto the particulate material (100) on said substrate, and then a further substrate with particulate material (210) may be placed thereon, typically such that said latter particulate material (100) contacts said coversheet.

Some embodiments of the invention relates to a pack comprising a multitude of at least five absorbent articles, as described below, comprising each an absorbent structure (herein referred to as absorbent core) produced by use of the method of the invention and/or by use of the apparatus of the invention, typically at a line speed as described above. The apparatus and method of the invention are such that very accurate filling of the reservoirs and very accurate transfer is achieved, even at high speed. The resulting absorbent cores, including a web of such cores that is subsequently separated into individual cores, are therefore substantially identical.

Of each of the absorbent article of the multitude of articles, comprises an absorbent core obtained by use of the method or the apparatus (1) of the invention, and each core comprises particulate polyacrylate/polyacrylic acid polymeric material, as described herein above, typically such crosslinked polymers, having internal and/or surface crosslinking. The multitude may of 5 articles, or of course it may be more than five absorbent articles, for example at least 10 absorbent articles. Typically, within a pack, the articles are consecutively produced articles. Thus, in some embodiments, the absorbent cores of said multitude are consecutively produced absorbent cores, produced by the method and/or apparatus of the invention.

The pack may be any pack, of any shape, and made of any packaging material, as known in the art, including a plastic bag, cardboard box etc.

Each absorbent core comprises (in addition to said particulate polymeric material) a nonwoven substrate material (110) and an adhesive material, adhering said particulate polymers to said substrate material and/or to one another, as described herein. In some embodiments, more than one adhesive material may be used. It may comprise more than one substrate material, and/or addition core cover materials, e.g. nonwovens, as described herein above. In some embodiments, the absorbent core may consist of said particulate material, adhesive material(s) and substrate material(s), and optional additional core cover materials.

Each absorbent core has a length dimension (in MD) and a width dimension (CD; perpendicular to the MD direction), each absorbent core is dividable in at least 10 strips extending along the width (in CD) of the core and each strips having a dimension in MD of 1.0 cm; the method below describes how such strips can be obtained from an absorbent core. Each absorbent core has at least 10 such strips and each core has at least 10 such strips that each have an "internal basis weight" of at least 100 gsm, but preferably at least 150 gsm, or preferably at least 200 gsm, said internal basis weight the basis weight of the particulate polyacrylate/polyacrylic acid polymeric material or of said particulate material and adhesive material(s), when present, but excluding said substrate material(s) and additional core cover materials.

For such multitude of absorbent articles, each having such an absorbent core, the average relative standard deviation of the amount of particulate polyacrylate/polyacrylic acid polymeric material is 10% or less, or 7% or less, or 5% or less, or 3% or less; this is the average over 10 relative standard deviations (% RSD, being average/standard deviation*100), each of said 10 being the % RSD of 5 equal strips (as defined below), each of which taken of one of the 5 articles, as defined and determined by the test method below. As set out below, the amount of AGM can be expressed in meq (AGM) or translated into grams (AGM).

This may be equally determined and applicable for multitudes of absorbent articles of more than 5, e.g. 10 or more, as set out below. When more than 5 articles are present, then the above average % RSD applies to at least 5 consecutive articles in the pack, but it may apply to more than 5 articles, or to more sets of 5 consecutive articles, or to all articles in the pack. Packs may in some embodiments comprise up to 100 articles, or up to 75 articles, or up to 50 articles.

The polyacrylic acid/polyacrylate polymeric material (AGM) herein may comprise other ingredients, such as coating agents; in any event, and in some embodiments herein, if such additional agents (e.g. coating agents) comprise acid/base groups, these agents are typically present at a level of less than 1% by weight of the AGM, and hence neglectable in the determination of the average % RSD. In another embodiment herein, the absorbent core comprises no other compounds that have acid or base croups other than the polyacrylic acid/polyacrylate polymer particles.

Because the method of the invention and the apparatus of the invention produce such cores with very accurate particulate material transfer to the substrate material, no lumps of access material are obtained. Hence reduced amounts of adhesive material may only be needed, for example such that the weight ratio of said particulate polyacrylate/polyacrylic acid polymers to said adhesive material (in said core) is from 15:1, or from 20:1, or from 25:1, to 100:1, or to 40:1 or to 40:1. It should be noted for the purpose of the absorbent articles of the invention, that the adhesive material(s) generally do not comprise any significant amount of acid or base group containing components Separately, or in addition, because the transfer of the particulate material is very accurate, the basis weight of the substrate material may be reduced, for example such that it has a basis weight of 15 gsm or less, or preferably 12 gsm or less, or 10 gsm or less.

The process herein is preferably a high speed process, as described herein; therefore, said absorbent articles comprises typically machine-readable registration marks, for example comprised on said substrate material, and/or on the topsheet, backsheet and/or any other component of said absorbent article. Such registration marks, known in the art, enable exact positioning of components of the a article during the manufacturing process with respect to said registration marks and/or to one another.

The amount of a particulate polymeric material (AGM) per strip and/or per surface area, e.g. the basis weight thereof, may vary along (MD); the absorbent core may be a so-called profiled core, whereby certain strips have a higher (internal or AGM) basis weight than another strip. It may be profiled in thickness direction; and/or the core may also profiled in CD direction, being a shaped core having a width dimension that varies, for example having a smaller width in the centre of the core, than in the average width in the front quarter and/or back quarter of the product.

Method to Determine Average Relative Standard Deviation

In this method, samples containing polyacrylate/polyacrylic acid based polymeric material (herein referred to as AGM) are first reacted with a known amount of HCl. An aliquot of the solution is then titrated to a bromophenol blue indicator with a NaOH solution. The titration results can be expressed as the milliequivalents (meq) of the neutralized acid groups of the AGM.

Of 5 absorbent articles of a multitude of absorbent articles (e.g. 5 or more or 10 or more), the absorbent cores produced by the method/apparatus of the invention are removed.

A first absorbent core is oriented such that the transverse (CD) edge that is in the article towards the front (of the user, e.g. front waist of a diaper) is labeled top, and the opposite transverse end is labeled bottom. The transverse and longitudinal axes are determined (and optionally marked on the core). The absorbent core is then cut in transversely extending (i.e. along full width) strips with an equal dimension in MD of 1.0 cm±0.01 cm; the last strip at the bottom may be less than 1 cm, but it in that case disregarded for this test.

A cutting die is used with a hydraulic press to section the core into such strips. The die is manufactured such that it is able to cut strips over the entire length (MD) and width (CD) and thickness of the core. The die is placed on an even surface (work bench) with its cutting blades facing upward, and the core is laid across the die centered along its transverse and longitudinal axes. A 0.25 inch Lexan plate with MD and CD dimensions larger than the die is placed on top of the core and then the assembly is placed in the hydraulic press and cut. The strips remain contained within the die until analysis to ensure that no AGM particles are lost. Each strip is labeled with a consecutive number (1 at top, 2, 3, 4, etc).

Each strip has thus a MD dimension of 1.0 cm, but the strips may have different (average) widths (average per strip). For the purpose of the invention, there are at least 10 strips per core.

For this first absorbent core, the "internal basis weight", as defined above, per strip is determined, by determining for each strip of said first core the surface area of said strip (1.0×CD dimension), and then removing the substrate material(s) (and other core cover materials, if present), as described herein, to obtain only the material(s) inside the absorbent core, i.e. the particulate polyacrylic acid/polyacrylate polymeric material transferred by the process/apparatus of the invention and optional adhesive material(s), if present. The weight of this material(s) is determined per strip, and then the "internal" basis weight per strip can be calculated (being the weight of said polymeric material and optional adhesive material per surface area of the strip).

Then, the 10 strips with highest "internal; basis weight" are determined for said first absorbent core. For the purpose of this test and this invention, there should be at least 10 strips that have an internal basis weight of at least 100 gsm (or preferably at least 150 gsm or at least 200 gsm as described herein above). The other strips (if any) are disregarded for the titration test below.

Said 10 strips are then submitted to the titration, described below. (For example strips 4, 5, 6, 7, 8, 9, 10, 12, 14, and 15.)

The remaining 4 absorbent cores of the remaining (e.g. selected) 4 absorbent articles (of the multitude) are each separately cut with the die exactly as set out above for the first absorbent core. Then, per absorbent core, the same strips as said 10 strips with highest internal basis weight are separately removed from the die and separately submitted to the titration method below. (For example strips 4, 5, 6, 7, 8, 9, 10, 12, 14, and 15, per core). Thus a total of 50 strips are obtained and separately submitted to titration.

Titration Method:

A 50 mL certified digital burette (e.g. Digitrate, Jencons Scientific, Bridgeville, Pa., or equivalent) is used for the titration. 0.1N HCl and 0.1N NaOH solutions are used (Baker Analyzed certified volumetric solutions; J. T. Baker, Phillipsburg, N.J.).

An individual strip is removed from the die placed into a 400 mL beaker and the substrate material(s) and optional other core cover materials are removed, ensure no loss of AGM during this transfer or substrate removal takes place. The remaining sample is herein referred to as "AGM".

Using a Class A volumetric pipet, 250 mL of 0.1N HCl acid is added, the AGM is submerged and soaked with stirring for 30 minutes. Then, this is filtered through a Whatman #4 filter paper into another 350 mL beaker. Using a Class A volumetric pipet, 25 mL aliquot of the filtered solution is pipeted into a 50 mL beaker. Four drops of 1% bromophenol blue indicator (w/w in deionized water) is added, and the solution is titrated with 0.1N NaOH to a blue endpoint. The volume of titrant is recorded to ±0.01 mL.

Each of the strips above (in total 50) is measured in like fashion.

Millequivalents of the neutralized AGM acid groups can be calculated per strip as:

$$\text{meq}(AGM)=2.5 \text{ meq(HCl)}-[\text{mL } 0.1N \text{ NaOH}*0.1 \text{ meq}/1 \text{ mL}]$$

This value in meq (AGM) can be translated into grams (AGM), as known in the art, if desired Then, the standard deviation over 5 strips of same number (e.g. the strips no. 4 of the 5 cores) can be determined and the relative standard deviation (% RSD, being average/standard deviation*100) between said equal strips (e.g. no. 4) of 5 articles.

This is determined for each set of 5 strips of the same number, to obtain a total of 10 standard deviations and 10 relative standard deviation (e.g. for strips 4, 5, 6, 7, 8, 9, 10, 12, 14, 15).

Then the average of said 10 relative standard deviations (% RSD) is calculated and reported as "average relative standard deviation" (average % RSD), as claimed herein. For the purpose of the invention, this should be 10% or less, but preferably 7% or less, or 5% or less.

The above test may be done for any multitude of absorbent articles of the invention, by taking 5 consecutive articles and cores thereof of a pack; the test may also be done in the same manner as set out above for more than 5 articles.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood, for the purpose of the invention, that the Figures are not to scale and that furthermore the dimensions of the exemplified apparatus and elements thereof, the dimensions of the particulate material, and said dimensions relative to one another, as depicted in the Figures are not intended to reflect the true dimensions of said elements or particulate material, or relative dimensions thereof, unless stated otherwise.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for making a structure that comprises particulate material supported or enclosed by a substrate material, the apparatus comprising:
    a first endless surface comprising a reservoir and adapted to move in a direction of movement;
    a particulate material feeder positioned adjacent the first endless surface and adapted to deposit particulate material to the reservoir;
    a second endless surface positioned adjacent the first endless surface and adapted to receive particulate material from the reservoir;
    a three-dimensional plate positioned adjacent the particulate material feeder and adjacent the first endless surface, the three-dimensional plate adapted to guide particulate material into the reservoir and to apply pressure on the particulate material, the three-dimensional plate comprising a plate face comprising a first surface area connected with a second surface area; and
    wherein the first surface area is substantially parallel to the first endless surface, wherein the second surface area is positioned downstream in the direction of movement from the first surface area, wherein the second surface area defines an angle from about 10° to about 80° with respect to the first endless surface.

2. The apparatus of claim 1, wherein the plate face comprises a third surface area positioned downstream in the direction of movement from the second surface area, the third surface area being substantially parallel to the first endless surface and in closer proximity to first endless surface than the first surface area.

3. The apparatus of claim 1, wherein the three-dimensional plate comprises a second plate face connected with the first surface area of the first plate face.

4. The apparatus of claim 3, wherein the second plate face is separated from the first surface area of the first plate face by an angle from about 60° to about 120°.

5. The apparatus of claim 3, wherein the particulate material feeder comprises a wall that opposes the second plate face, wherein the wall and the second plate face guide particulate material toward the first endless surface.

6. The apparatus of claim 1, wherein the first surface area and the second surface area each comprise an average length dimension of at least about 2 mm in the direction of movement.

7. The apparatus of claim 1, wherein the first plate face comprises a width substantially equal to a width of the first endless surface.

8. The apparatus of claim 1, further comprising a drum comprising an outer surface defining the first endless surface, the drum comprising a drum radius.

9. The apparatus of claim 8, wherein the first surface area of the first plate face is curved and having a curvature comprising a plate face radius, the ratio of the drum radius to the plate face radius is from about 8:10 to about 10:8.

10. The apparatus of claim 1, further comprising a pressure control means connected with the three-dimensional plate, the pressure control means for controlling the external pressure applied by the three-dimensional plate on the particulate material.

11. The apparatus of claim 10, wherein the external pressure is from about 1.5 bar to about 3 bar.

12. The apparatus of claim 10, wherein the pressure control means varies an average distance between the first surface area of the first plate face and the first endless surface.

13. The apparatus of claim 10, wherein the pressure control means comprises an actuator that senses a pressure on the three-dimensional plate, and in response thereto, adjusts a position of the three-dimensional plate relative to the first endless surface, by moving the three-dimensional plate toward or away from the first endless surface.

14. The apparatus of claim 13, wherein the actuator senses the pressure on the first plate face by the particulate material.

15. The apparatus of claim 1, wherein the reservoir comprises an average depth from about 1.0 mm to about 8.0 mm.

16. The apparatus of claim 1, wherein the particulate material feeder comprises an opening to allow exit of the particulate material to the first endless surface, wherein the opening comprises a dimension in the direction of movement from about 10 mm to about 140 mm.

* * * * *